US012169930B2

(12) United States Patent
Masuda et al.

(10) Patent No.: US 12,169,930 B2
(45) Date of Patent: Dec. 17, 2024

(54) MEDICAL INFORMATION PROCESSING APPARATUS, MEDICAL INFORMATION PROCESSING METHOD, AND STORAGE MEDIUM

(71) Applicants: Canon Kabushiki Kaisha, Tokyo (JP); CANON MEDICAL SYSTEMS CORPORATION, Tochigi (JP)

(72) Inventors: Yukiteru Masuda, Kawasaki (JP); Gakuto Aoyama, Nasushiobara (JP)

(73) Assignees: Canon Kabushiki Kaisha, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 565 days.

(21) Appl. No.: 17/503,748

(22) Filed: Oct. 18, 2021

(65) Prior Publication Data

US 2022/0138940 A1 May 5, 2022

(30) Foreign Application Priority Data

Oct. 30, 2020 (JP) .................................. 2020-182284

(51) Int. Cl.
 G06T 7/12 (2017.01)
 A61B 6/03 (2006.01)
 (Continued)

(52) U.S. Cl.
 CPC ............ G06T 7/0012 (2013.01); A61B 6/032 (2013.01); A61B 6/503 (2013.01); G06T 7/11 (2017.01);
 (Continued)

(58) Field of Classification Search
 CPC . G06T 7/0012; G06T 7/11; G06T 7/60; G06T 2207/30048; G06T 2207/30168; G06V 10/26; A61B 6/032; A61B 6/503
 (Continued)

(56) References Cited

U.S. PATENT DOCUMENTS

2011/0170755 A1* 7/2011 Buelow ................. G06T 7/0012
 382/128
2012/0232386 A1* 9/2012 Mansi ..................... G06T 19/00
 600/437

(Continued)

FOREIGN PATENT DOCUMENTS

JP 2019-202142 A 11/2019

OTHER PUBLICATIONS

Japanese Office Action issued Feb. 6, 2024 in Japanese Patent Application No. 2020-182284, 3 pages.

*Primary Examiner* — Michael R Neff
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry is configured to obtain medical images taken at a plurality of points in time. The processing circuitry is configured to obtain structures of a plurality of tissues, from medical images taken at a first point in time and at a second point in time different from the first point in time among the plurality of points in time. The processing circuitry is configured to calculate a measurement value related to a contact part between the plurality of tissues at the first point in time, on the basis of the obtained structures of the plurality of tissues at the second point in time and the obtained structures of the plurality of tissues at the first point in time.

24 Claims, 12 Drawing Sheets

(51) Int. Cl.
  *A61B 6/50*  (2024.01)
  *G06T 7/00*  (2017.01)
  *G06T 7/11*  (2017.01)
  *G06T 7/60*  (2017.01)
  *G06V 10/26* (2022.01)

(52) U.S. Cl.
  CPC .............. *G06T 7/60* (2013.01); *G06V 10/26* (2022.01); *G06T 2207/30048* (2013.01); *G06T 2207/30168* (2013.01)

(58) Field of Classification Search
  USPC ......................................................... 382/128
  See application file for complete search history.

(56) References Cited

U.S. PATENT DOCUMENTS

| | | | |
|---|---|---|---|
| 2016/0171766 A1* | 6/2016 | Grbic ................... | A61B 17/00 345/423 |
| 2020/0155094 A1 | 5/2020 | Nishioka | |

* cited by examiner

FIG.5A

| CROSS-SECTION CONDITION SETTING | | |
|---|---|---|
| POSITION AT ○ [      ] mm ○ [      ] % | ☐ IN THE DIRECTION FROM ANTERIOR COMMISSURE TOWARD POSTERIOR COMMISSURE |
| POSITION AT ◉ [  30  ] mm ● [      ] % | ☒ IN THE DIRECTION FROM MIDDLE POINT TOWARD POSTERIOR COMMISSURE |
| POSITION AT ○ [      ] mm ○ [      ] % | ☐ IN THE DIRECTION FROM MIDDLE POINT TOWARD ANTERIOR COMMISSURE |

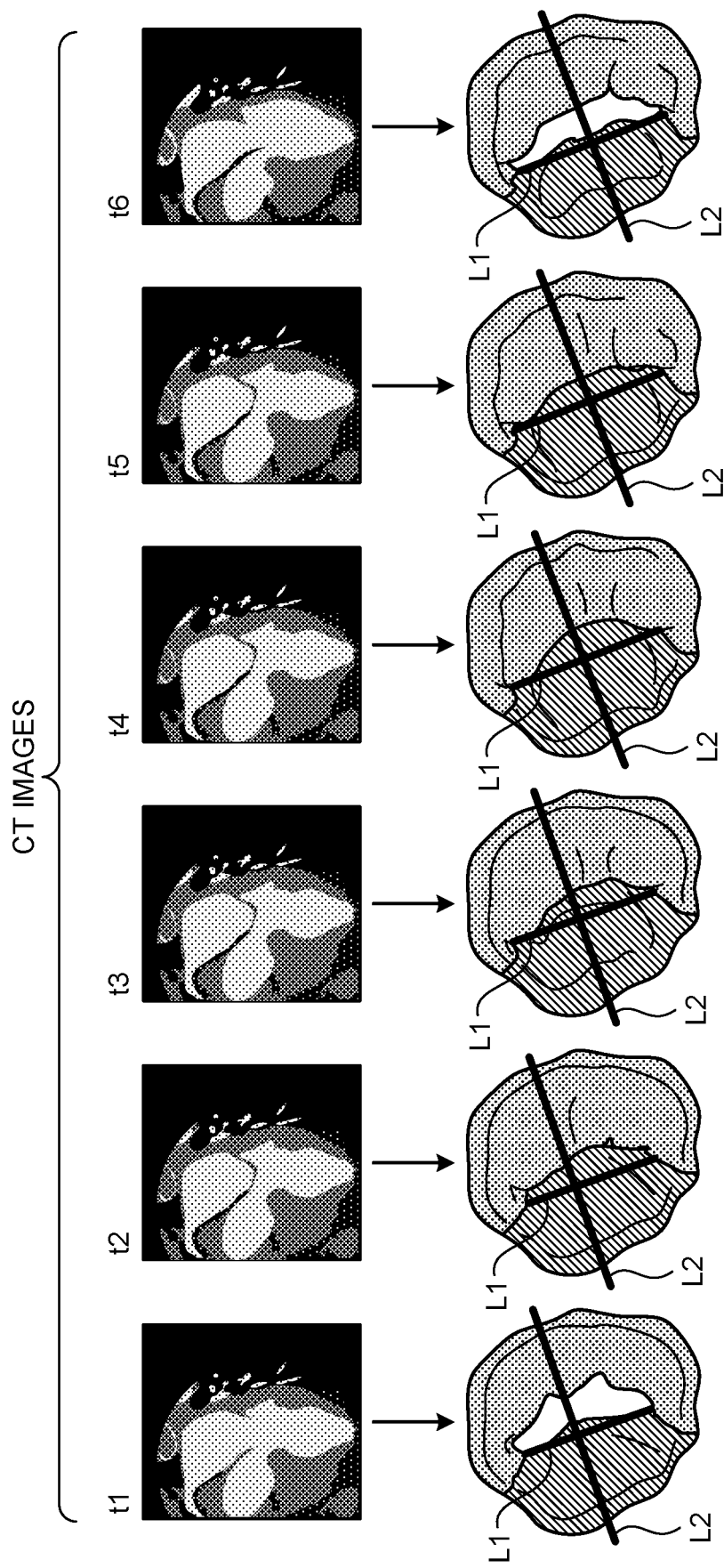

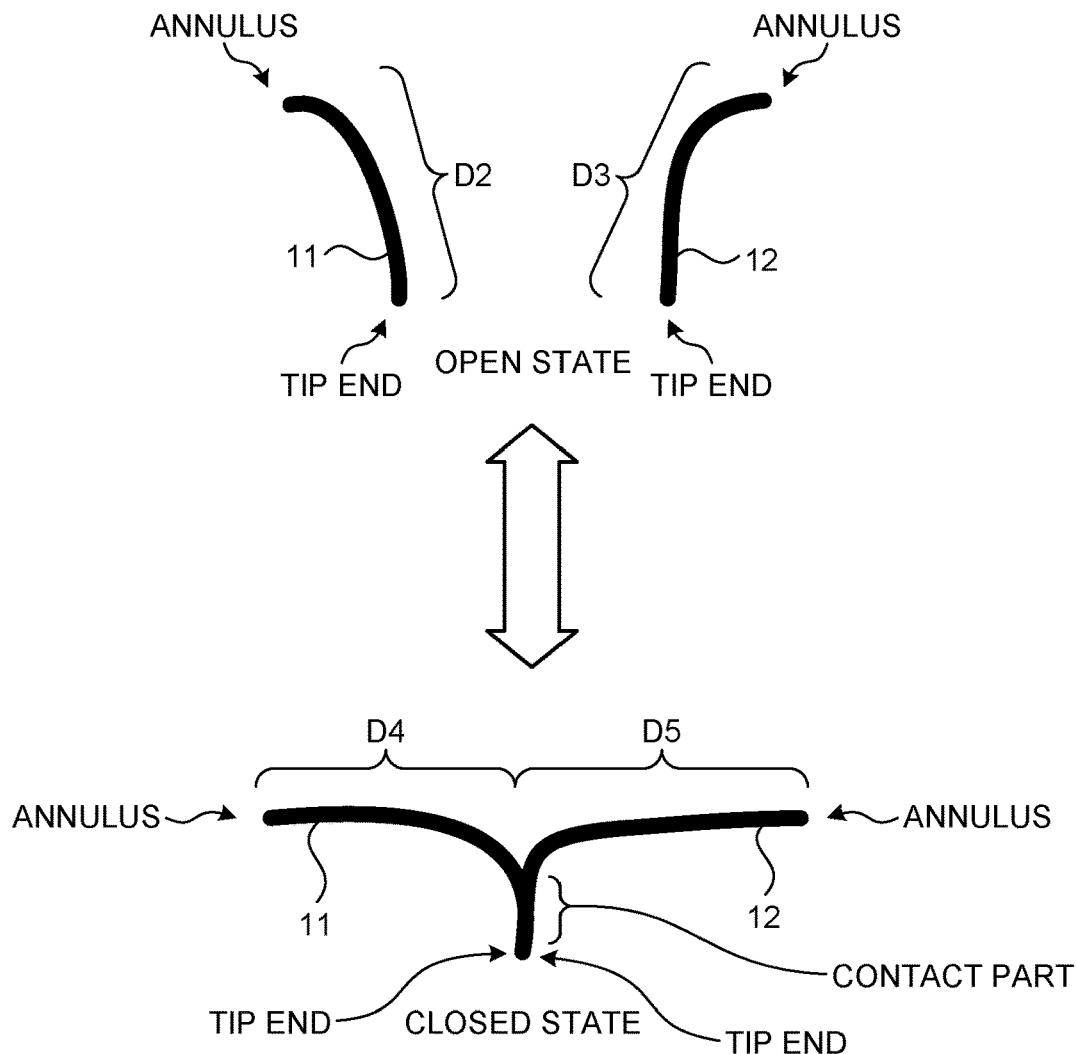

| CROSS-SECTION POSITION | ANTERIOR CUSP REPRESENTATIVE VALUES | | POSTERIOR CUSP REPRESENTATIVE VALUES | | LENGTH OF CONTACT PART |
|---|---|---|---|---|---|
| | OPEN STATE | CLOSED STATE | OPEN STATE | CLOSED STATE | |
| L2-1 | 10 | 6 | 6 | 4 | 2 |
| L2-2 | 12 | 8 | 8 | 3 | 4 |
| L2-3 | 15 | 10 | 10 | 5 | 5 |
| L2-4 | 10 | 6 | 8 | 5 | 3 |
| L2-5 | 8 | 3 | 8 | 3 | 5 |
| AVERAGE | 11 | 6.6 | 8 | 4 | 3.8 |
| TOTAL | 55 | 33 | 40 | 20 | 19 |

# MEDICAL INFORMATION PROCESSING APPARATUS, MEDICAL INFORMATION PROCESSING METHOD, AND STORAGE MEDIUM

CROSS-REFERENCE TO RELATED APPLICATIONS

This application is based upon and claims the benefit of priority from Japanese Patent Application No. 2020-182284, filed on Oct. 30, 2020; the entire contents of which are incorporated herein by reference.

FIELD

Embodiments described herein relate generally to a medical information processing apparatus, a medical information processing method, and a storage medium.

BACKGROUND

Conventionally, to diagnose the state of a disease of a heart valve such as the aortic valve or the mitral valve, the length of a contact part between valve leaflets (the part where the valve leaflets are in contact with each other while the valve is in a closed state) is measured. Known measuring methods include a method by which, for example, the valve leaflets are segmented from a medical image rendering the heart valve, so as to directly measure the length of the contact part between the segmented valve leaflets.

BRIEF DESCRIPTION OF THE DRAWINGS

FIG. 5A is a drawing for explaining an example of a condition setting related to setting a cross-section position according to the first embodiment;

FIG. 6 is a drawing illustrating an example of a cross-section setting process performed by the setting function according to the first embodiment;

FIG. 7 is a drawing for explaining a calculating process performed by a calculating function according to the first embodiment;

FIG. 8 is a drawing for explaining an example of condition settings related to determining representative values according to the first embodiment;

DETAILED DESCRIPTION

Figure 1:
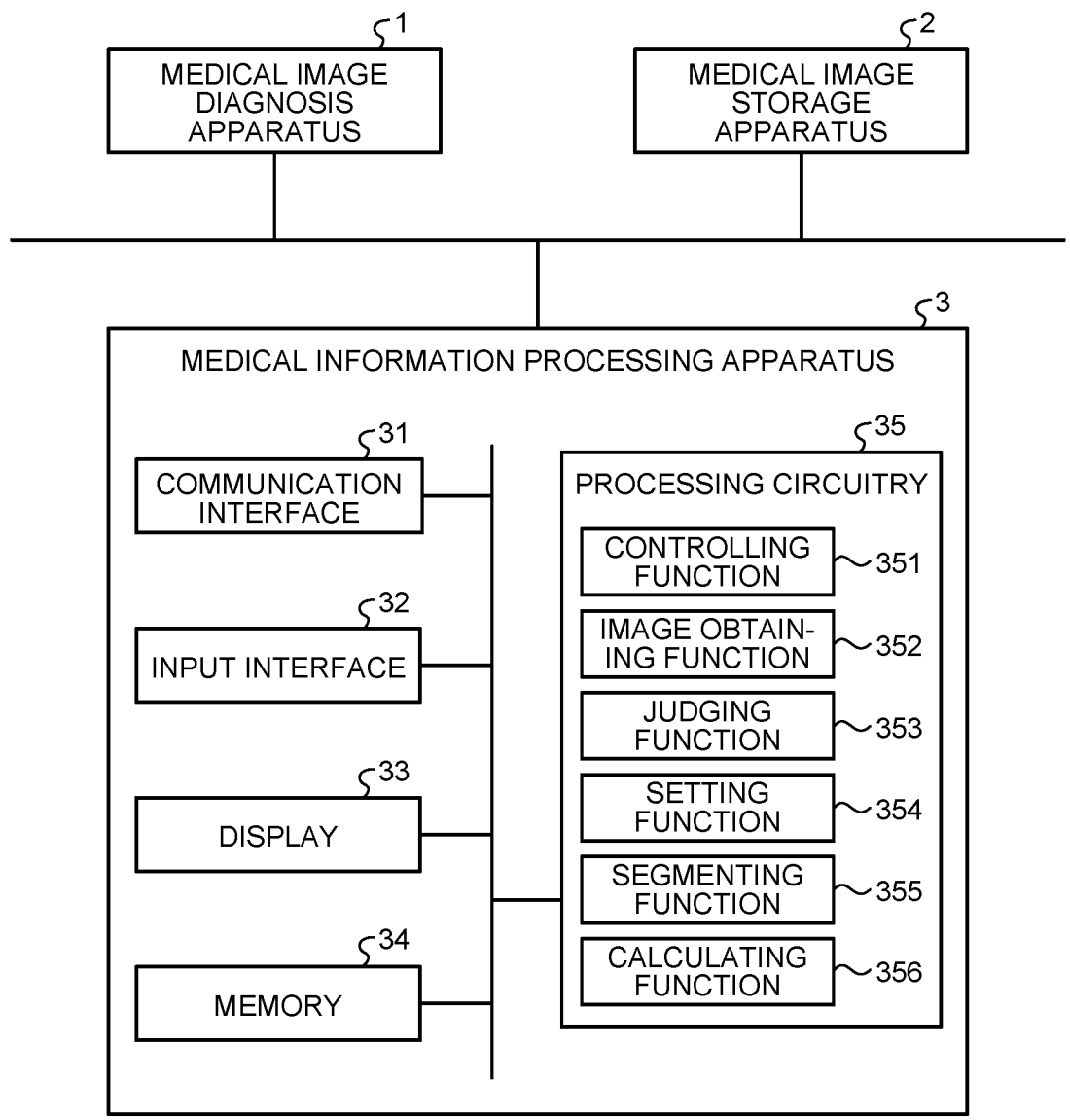
FIG. 1 is a diagram illustrating an exemplary configuration of a medical information processing apparatus according to a first embodiment.

A medical information processing apparatus according to an embodiment includes processing circuitry. The processing circuitry is configured to obtain medical images taken at a plurality of points in time. The processing circuitry is configured to obtain structures of a plurality of tissues, from medical images taken at a first point in time and at a second point in time different from the first point in time among the plurality of points in time. The processing circuitry is configured to calculate a measurement value related to a contact part between the plurality of tissues at the first point in time, on the basis of the obtained structures of the plurality of tissues at the second point in time and the obtained structures of the plurality of tissues at the first point in time.

Exemplary embodiments of a medical information processing apparatus, a medical information processing method, and a storage medium will be explained in detail below, with reference to the accompanying drawings. The medical information processing apparatus, the medical information processing method, and the storage medium of the present disclosure are not limited to the embodiments described below. Further, it is possible to combine any of the embodiments with another embodiment or a conventional technique as long as no conflict occurs in the processing. Further, in the description below, some of the constituent elements that are the same as each other will be referred to by using the same reference characters, and the duplicate explanations thereof will be omitted.

First Embodiment

FIG. 1 is a diagram illustrating an exemplary configuration of a medical information processing apparatus according to a first embodiment. For example, as illustrated in FIG. 1, a medical information processing apparatus 3 according to the present embodiment is communicably connected to a medical image diagnosis apparatus 1 and a medical image storage apparatus 2 via a network. To the network illustrated in FIG. 1, other various types of apparatuses, devices, and systems may be connected.

The medical image diagnosis apparatus 1 is configured to image an examined subject (hereinafter, "patient") and to generate medical images. Further, the medical image diagnosis apparatus 1 is configured to transmit the generated medical images to any of the various types of apparatuses and devices in the network. For example, the medical image diagnosis apparatus 1 may be an X-ray diagnosis apparatus, an X-ray Computed Tomography (CT) apparatus, a Magnetic Resonance Imaging (MRI) apparatus, an ultrasound diagnosis apparatus, a Single Photon Emission Computed Tomography (SPECT) apparatus, or a Positron Emission computed Tomography (PET) apparatus.

The medical image storage apparatus 2 is configured to store therein various types of medical images related to the patient. More specifically, the medical image storage apparatus 2 is configured to obtain the medical images from the medical image diagnosis apparatus 1 via the network and to store the medical images by having the medical images saved in a memory provided in the medical image storage apparatus 2. For example, the medical image storage apparatus 2 may be realized by using a computer device such as a server or a workstation. Further, for example, the medical image storage apparatus 2 may be realized by using a Picture Archiving and Communication System (PACS) so as to store therein the medical images in a format compliant with a Digital Imaging and Communications in Medicine (DICOM) scheme.

The medical information processing apparatus 3 is configured to perform various types of information processing processes related to the patient. More specifically, the medical information processing apparatus 3 is configured to obtain a medical image from either the medical image diagnosis apparatus 1 or the medical image storage apparatus 2 via the network and to perform the various types of information processing processes by using the medical image. For example, the medical information processing apparatus 3 may be realized by using a computer device such as a server or a workstation.

For example, the medical information processing apparatus 3 includes a communication interface 31, an input interface 32, a display 33, a memory 34, and processing circuitry 35.

The communication interface 31 is configured to control various types of data transfer transmitted and received between, and communication performed between, the medical information processing apparatus 3 and any of the other apparatuses and devices connected via the network. More specifically, the communication interface 31 is connected to the processing circuitry 35 and is configured to output the data received from any of the other apparatuses and devices to the processing circuitry 35 and to transmit the data output from the processing circuitry 35 to any of the other apparatuses and devices. For example, the communication interface 31 may be realized by using a network card, a network adaptor, or a Network Interface Controller (NIC).

The input interface 32 is configured to receive operations to input various types of instructions and various types of information from a user. More specifically, the input interface 32 is connected to the processing circuitry 35 and is configured to convert the input operations received from the user into electrical signals and to output the electrical signals to the processing circuitry 35. For example, the input interface 32 may be realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 32 does not necessarily have to include physical operation component parts such as a mouse, a keyboard, and/or the like. For instance, possible examples of the input interface 32 include an electrical signal processing circuit configured to receive an electrical signal corresponding to an input operation from an external input device provided separately from the apparatus and to output the electrical signal to a controlling circuit.

The display 33 is configured to display various types of information and various types of data. More specifically, the display 33 is connected to the processing circuitry 35 and is configured to display the various types of information and the various types of data output from the processing circuitry 35. For example, the display 33 may be realized by using a liquid crystal display, a Cathode Ray Tube (CRT) display, a touch panel, or the like.

The memory 34 is configured to store therein various types of data and various types of programs. More specifically, the memory 34 is connected to the processing circuitry 35 and is configured to store therein data input thereto from the processing circuitry 35 and to read and output the stored data to the processing circuitry 35. For example, the memory 34 is realized by using a semiconductor memory element such as a Random Access Memory (RAM) or a flash memory, or a hard disk, an optical disk, or the like.

The processing circuitry 35 is configured to control the entirety of the medical information processing apparatus 3. For example, the processing circuitry 35 is configured to perform various types of processes in accordance with the input operations received from the user via the input interface 32. For example, the processing circuitry 35 is configured to receive the data transmitted thereto from another apparatus or device via the communication interface 31 and to store the received data into the memory 34. Further, for example, from the memory 34, the processing circuitry 35 is configured to output the received data to the communication interface 31 so as to transmit the data to another apparatus or device. Further, for example, the processing circuitry 35 is configured to cause the display 33 to display the data received from the memory 34.

The exemplary configuration of the medical information processing apparatus 3 according to the present embodiment has thus been explained. For example, the medical information processing apparatus 3 according to the present embodiment is installed in a medical facility such as a hospital or a clinic and is configured to assist the user such as a medical doctor with performing various types of diagnosing processes and making treatment plans. For example, the medical information processing apparatus 3 is configured to perform various types of processes so that a measuring process related to a contact part of a heart valve is performed more accurately.

As mentioned above, the known measuring methods related to the contact part of a heart valve include the method by which the valve leaflets are segmented from a medical image rendering the heart valve, so as to directly measure the length (called "coaptation height") of the contact part between the segmented valve leaflets. However, according to this method, when the medical image being used has a low temporal resolution and/or a low spatial resolution, it may not be possible to accurately obtain the structures of the valve leaflets, and it may be difficult in some situations to directly calculate measurement information of the valve leaflets.

For example, while a heart valve is open (in an open state), because the tip end of the heart valve makes small movements due to the blood flow, the tip end of the heart valve rendered in a medical image having a low temporal resolution would be blurry due to the insufficient temporal resolution, which would make it impossible to understand the structure accurately. Also, for example, while a heart valve is closed (in a closed state), an insufficient spatial resolution would make it impossible to understand the structure of each of the valve leaflets, in a section underneath the contact part between the valve leaflets. In other words, in the heart valve in the closed state, it would be impossible to recognize the contact part where the valve leaflets are in contact with each other, from the part where the valve leaflets ate not in contact with each other on the tip end side of the valve. It would therefore be impossible to understand the structures of the valve leaflets. Consequently, it might be difficult in some situations to directly measure the length of the contact part between the valve leaflets from the medical images.

To cope with these situations, the medical information processing apparatus 3 according to the present embodiment is configured to be able to accurately perform a measuring process relevant to the contact part, by performing a measuring process relevant to the contact part between a plurality of tissues in the patient's body (e.g., valve leaflets of a heart valve) (hereinafter, simply "tissues"), while using the structures of the plurality of tissues rendered in medical images taken at a plurality of points in time (hereinafter, simply "time points").

More specifically, by using the plurality of medical images taken at times at which the states of the plurality of tissues are different from each other, the medical information processing apparatus 3 is configured to obtain the structures of the plurality of tissues in each of the states and to calculate a measurement value related to the contact part on the basis of the obtained structures of the plurality of tissues in each of the states. For example, on the basis of the medical images of the heart valve in an open state and a closed state, the medical information processing apparatus 3 is configured to obtain the structures of the valve leaflets in the open state and the structures of the valve leaflets in the closed state and to further measure the length of the contact part between the valve leaflets in the closed state by using each of the obtained structures. In the following sections, the medical information processing apparatus 3 configured in this manner will be explained in detail.

For example, as illustrated in FIG. 1, in the present embodiment, the processing circuitry 35 of the medical information processing apparatus 3 is configured to execute a controlling function 351, an image obtaining function 352, a judging function 353, a setting function 354, a segmenting function 355, and a calculating function 356. In the present example, the controlling function 351 is an example of a display controlling unit. The image obtaining function 352 is an example of an image obtaining unit. The segmenting function 355 is an example of a structure obtaining unit. The calculating function 356 is an example of a calculating unit.

The controlling function 351 is configured to exercise control so that various types of Graphical User Interfaces (GUIs) and various types of display information are generated and displayed on the display 33, in accordance with operations performed via the input interface 32. For example, the controlling function 351 is configured to cause the display 33 to display a GUI used for setting a condition under which the measurement values related to the contact part are to be calculated, as well as display information based on the calculated measurement values. Also, the controlling function 351 is capable of generating various types of display images on the basis of medical images obtained by the image obtaining function 352. The GUIs and the display information displayed as a result of processes performed by the controlling function 351 will be explained in detail later.

The image obtaining function 352 is configured to obtain, via the communication interface 31, medical images of the patient from either the medical image diagnosis apparatus 1 or the medical image storage apparatus 2. More specifically, the image obtaining function 352 is configured to obtain the medical images which have structures including the plurality of tissues and the plurality of states and which contain morphological information about a site in which the structures including the plurality of tissues are in contact with each other. More specifically, the image obtaining function 352 is configured to obtain a plurality of medical images which contain the morphological information about anatomical structures of the tissues subject to the processing and in which the tissues are in mutually-different states. Further, the image obtaining function 352 is also capable of obtaining a plurality of medical images containing functional information of the tissues subject to the processing.

In this situation, as the plurality of medical images in which the tissues are in the mutually-different states, the image obtaining function 352 may obtain a plurality of medical images acquired by imaging the tissues multiple times in a time direction two-dimensionally or three-dimensionally or may obtain medical images taken of the tissues in a first state and the tissues in a second state during mutually-different medical examinations.

For example, as the plurality of medical images described above, the image obtaining function 352 is configured to obtain CT images, ultrasound images, MRI images, X-ray images, Angiography images, PET images, or SPECT images. In the present embodiment, an example will be explained in which four-dimensional CT images that are three-dimensionally taken multiple times in the time direction are obtained.

With respect to the plurality of medical images obtained by the image obtaining function 352, the judging function 353 is configured to judge the states of the plurality of tissues rendered in the medical images. More specifically, with respect to the plurality of medical images, the judging function 353 is configured to judge the states of the plurality of tissues of which contact states change over the course of time. For example, the judging function 353 judges, with respect to the heart valve rendered in the medical images, whether the heart valve belongs to a state of being open (an open state) or the heart valve belongs to a state of being closed (a closed state). Processes performed by the judging function 353 will be explained in detail later.

With the plurality of tissues, the setting function 354 is configured to set a cross-section subject to the measuring process related to the contact part. More specifically, the setting function 354 is configured, with respect to each of the plurality of medical images obtained by the image obtaining function 352, to set a cross-section rendering the contact part between the plurality of tissues. Processes performed by the setting function 354 will be explained in detail later.

The segmenting function 355 is configured to segment structures of interest with respect to each of the plurality of medical images obtained by the image obtaining function 352. More specifically, with respect to each of the plurality of medical images obtained by the image obtaining function 352, the segmenting function 355 is configured to segment the structure subject to the measuring process related to the contact part. For example, the segmenting function 355 segments the heart valve (e.g., both the anterior cusp and the posterior cusp of the mitral valve) from the cross-section set in each of the plurality of medical images obtained by the image obtaining function 352. Processes performed by the segmenting function 355 will be explained in detail later.

The calculating function 356 is configured to calculate the measurement values related to the contact part between the plurality of tissues. More specifically, the calculating function 356 is configured to calculate the measurement values related to the contact part between the plurality of tissues on the basis of the structures of the plurality of tissues segmented from the plurality of medical images taken at the mutually-different time points. In other words, the calculating function 356 is configured to calculate the measurement values of the structures (the structures of interest) subject to the measuring process related to the contact part between the plurality of tissues. For example, the calculating function 356 calculates the measurement values related to the contact part in the closed state, by using the structures of the plurality of tissues in the open state (the structures of interest in the open state) and the structures of the plurality of tissues in the closed state (the structures of interest in the closed state). Processes performed by the calculating function 356 will be explained in detail later.

The processing circuitry 35 described above is realized by using a processor, for example. In that situation, the processing functions described above are stored in the memory 34 in the form of computer-executable programs. Further, the processing circuitry 35 is configured to realize the functions corresponding to the programs, by reading and executing the programs stored in the memory 34. In other words, the processing circuitry 35 that has read the programs has the processing functions illustrated in FIG. 1.

Further, it is also acceptable to structure the processing circuitry 35 by combining together a plurality of independent processors, so that the processing functions are realized as a result of the processors executing the programs. Further, the processing functions of the processing circuitry 35 may be realized as being distributed among or integrated into one or more processing circuits, as appropriate. Also, the processing function of the processing circuitry 35 may be realized by a combination of hardware such as circuitry and software. Furthermore, although the example was explained above in which the programs corresponding to the processing functions are stored in the single storage circuit (i.e., the memory 34), possible embodiments are not limited to this example. For instance, it is also acceptable to store the programs corresponding to the processing functions in a plurality of storage circuits in a distributed manner, so that the processing circuitry 35 reads and executes the programs from the storage circuits.

Figure 2:
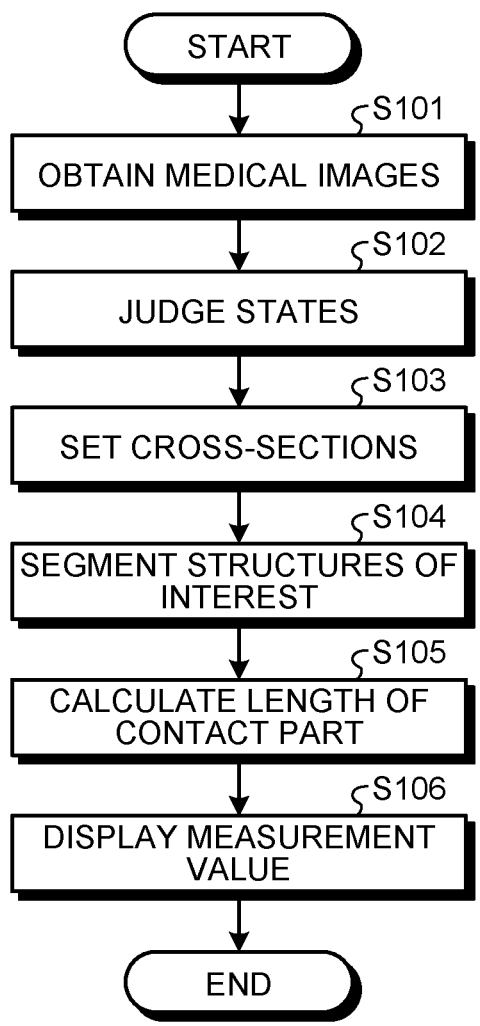
FIG. 2 is a flowchart illustrating a processing procedure of processes performed by processing functions included in processing circuitry of the medical information processing apparatus according to the first embodiment.

As explained above, the medical information processing apparatus 3 is configured to perform the measuring process related to the contact part between the plurality of tissues, by using the structures of the plurality of tissues (e.g., the valve leaflets of the heart valve) rendered in the medical images taken at the plurality of time points. Next, at first, a procedure in processes performed by the medical information processing apparatus 3 will be explained, with reference to FIG. 2. FIG. 2 is a flowchart illustrating the processing procedure of the processes performed by the processing functions included in the processing circuitry 35 of the medical information processing apparatus 3 according to the first embodiment.

For example, as illustrated in FIG. 2, in the present embodiment, the image obtaining function 352 obtains medical images of the patient from either the medical image diagnosis apparatus 1 or the medical image storage apparatus 2 (step S101). For example, in accordance with a medical image obtaining operation performed via the input interface 32, the image obtaining function 352 obtains the plurality of medical images which contain morphological information about anatomical structures of the tissues subject to the processing and in which the tissues are in mutually-different states. This process is realized, for example, as a result of the processing circuitry 35 invoking and executing a program corresponding to the image obtaining function 352 from the memory 34.

Subsequently, with respect to the obtained plurality of medical images, the judging function 353 judges the states of the plurality of tissues rendered in the medical images (step S102). This process is realized, for example, as a result of the processing circuitry 35 invoking and executing a program corresponding to the judging function 353 from the storage circuit 34.

After that, with respect to each of the obtained plurality of medical images, the setting function 354 sets a cross-section used for performing the measuring process related to the contact part (step S103). This process is realized, for example, as a result of the processing circuitry 35 invoking and executing a program corresponding to the setting function 354 from the memory 34.

Subsequently, with respect to each of the obtained plurality of medical images, the segmenting function 355 segments the structures of interest (the structures subject to the measuring process related to the contact part) on the set cross-section (step S104). This process is realized, for example, as a result of the processing circuitry 35 invoking and executing a program corresponding to the segmenting function 355 from the memory 34.

After that, the calculating function 356 calculates the measurement values related to the contact part between the plurality of tissues, on the basis of the structures of the plurality of tissues (e.g., the structures of interest on the set cross-section) segmented from the plurality of medical images taken at the mutually-different time points (step S105). This process is realized, for example, as a result of the processing circuitry 35 invoking and executing a program corresponding to the calculating function 356 from the memory 34.

Subsequently, the controlling function 351 causes the calculated measurement values to be displayed (step S106). This process is realized, for example, as a result of the processing circuitry 35 invoking and executing a program corresponding to the controlling function 351 from the memory 34.

Next, details of processes performed by the medical information processing apparatus 3 will be explained. In the following sections, an example will be explained in which a contact part in the mitral valve is to be measured. The medical image obtaining process:

As explained at step S101 in FIG. 2, the image obtaining function 352 obtains the plurality of medical images in which the tissues are in the mutually-different states, in accordance with the medical image obtaining operation performed via the input interface 32. For example, the image obtaining function 352 obtains four-dimensional CT images obtained by three-dimensionally imaging the mitral valve multiple times in the time direction.

In this situation, the medical image obtaining process at step S101 may start being performed according to an instruction from the user received via the input interface 32 as described above. Alternatively, the processes may be started automatically. In that situation, for example, the image obtaining function 352 is configured to monitor the medical image storage apparatus 2 and is configured, every time a new medical image is stored therein, to automatically obtain the medical image.

In this situation, the image obtaining function 352 may be configured to judge the newly-stored medical image on the basis of an obtaining condition set in advance so as to perform the obtaining process when the medical image satisfies the obtaining condition. For example, the memory 34 may store therein the obtaining condition used for judging the states of medical images, so that the image obtaining function 352 judges the newly-stored medical image on the basis of the obtaining condition stored in the memory 34.

In one example, the memory 34 may store therein an obtaining condition such as "obtain a medical image taken by using an imaging protocol intended for the heart", "obtain a medical image reconstructed in enlargement", or a combination of these two conditions. The image obtaining function 352 obtains medical images satisfying the obtaining condition. The state judging process:

As explained at step S102 in FIG. 2, with respect to the plurality of medical images, the judging function 353 determines the states of the plurality of tissues of which the contact states change over the course of time. For example, with respect to the four-dimensional CT images obtained by three-dimensionally imaging the mitral valve multiple times in the time direction, the judging function 353 judges whether the mitral valve in each of the CT images is in the open state or in the closed state.

Figure 3:
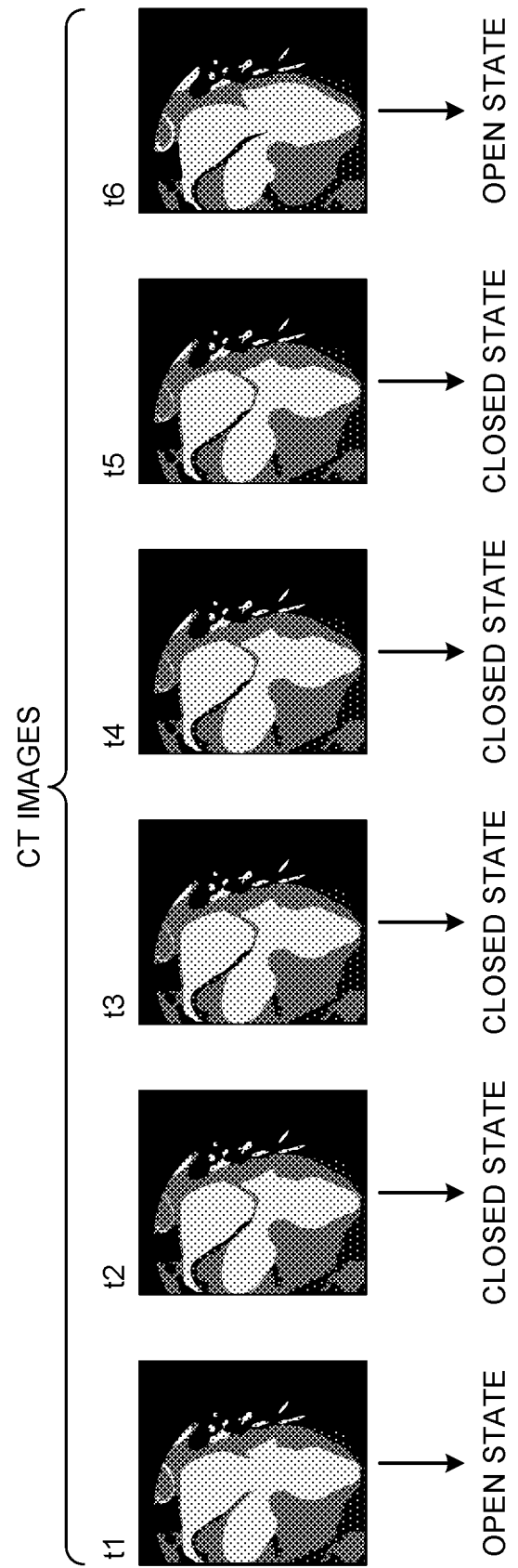
FIG. 3 is a drawing for explaining an example of a judging process performed by a judging function according to the first embodiment.

FIG. 3 is a drawing for explaining an example of the judging process performed by the judging function 353 according to the first embodiment. FIG. 3 illustrates the example in which the image obtaining function 352 has obtained CT images taken of the mitral valve at time points t1 to t6. For example, in principle, the mitral valve is open at time points between early systole and early diastole and is closed at time points between early diastole and late diastole of the heart. Accordingly, there are two states, namely, the open state and the closed state.

With respect to the mitral valve rendered in the CT images taken at the time points t1 to t6, the judging function 353 judges to which of the two states (i.e., the open state and the closed state) the mitral valve belongs. For example, as illustrated in FIG. 3, the judging function 353 determines that the CT images at the time points t1 and t6 correspond to the open state, whereas the CT images at the time points t2 to t5 correspond to the closed state.

In this situation, as the judging method, the judging function 353 may use any of various types of methods. Generally speaking, at the time of taking CT images of the heart, in many situations, electrocardiogram-synchronized imaging is performed in order to take images in synchronization with the movements of the heart, and electrocardiographic information during the imaging is stored in a DICOM header. Accordingly, for example, the judging function 353 is able to obtain the electrocardiographic information from the DICOM header and to identify the states on the basis of the electrocardiographic information. For example, while the duration of one heartbeat (an R-R interval) in an electrocardiogram is regarded as 100%, a relationship between different time points (percentage numerical values) and the states are determined in advance as conditions, so that the judging function 353 determines the states on the basis of the conditions. In one example, the judging function 353 determines that images reconstructed at the time points corresponding to 40% to 90% belong to the open state, whereas images reconstructed at the other time points belong to the closed state.

Further, as for the method for judging the states on the basis of electrocardiographic information, besides the abovementioned method by which the states are set with the time points corresponding to the predetermined percentages (%) in the R-R interval, it is also acceptable to use another method by which conditions are set with predetermined elapsed time periods (ms) since the time point of the first R-wave in the R-R interval. In other words, it is possible to determine the relationship between the elapsed time periods since the time point of the first R-wave in the R-R interval and the states as conditions, so that the judging function 353 determines the states on the basis of the conditions.

As yet another judging method, it is also acceptable to use a method by which, for example, heart sounds are simultaneously recorded while the CT images are taken, so as to determine the open state and the closed state of the mitral valve on the basis of information about the heart sounds. Also, as yet another judging method, for example, it is also acceptable to use a method by which the shape of the mitral valve is obtained by using any of known region segmentation techniques, so as to determine the open state and the closed state on the basis of the shape. In that situation, examples of the known region segmentation techniques include Otsu's binarization method based on CT values, a region growing method, a snake method, a graph cut method, and a mean shift method.

Further, yet another method is also acceptable by which the open state and the closed state are determined by using a learning model that is reconstructed on the basis of training-purpose data prepared in advance with the use of a machine learning technique (which may be deep learning) and is configured to indicate a relationship between the states of the images (conditions) and the states of the mitral valve.

Furthermore, the judging process may be performed on the basis of the shape of another tissue other than the mitral valve that is related to the states of the mitral valve. In that situation, for example, the volume of the left ventricle may be used. Because the volume of the left ventricle changes in accordance with the movements of the heart, it is possible to estimate cardiac phases and, in turn, movement states of the mitral valve on the basis of the volume.

Because the structure of the left ventricle is larger than that of the mitral valve, there is a possibility that the calculation may be more accurate than the direct estimation from the states of the mitral valve rendered in the images.

The judging methods described above are merely examples. In the present embodiment, it is possible to use any method for identifying the states of the tissues subject to the processing. For example, the user may manually designate the states via the input interface 32.

The Cross-Section Setting Process:

As explained at step S103 in FIG. 2, with respect to the plurality of medical images in which the states have been determined, the setting function 354 sets the cross-section used for performing the measuring process related to the contact part between the plurality of tissues. For example, with respect to each of the CT images which correspond to the time points t1 to t6 and in which the open state and the closed state of the mitral valve have been determined, the setting function 354 sets a cross-section (a two-dimensional cross-section on which the user wishes to perform the measuring process) used for performing the measuring process related to the contact part of the mitral valve.

Figure 4:
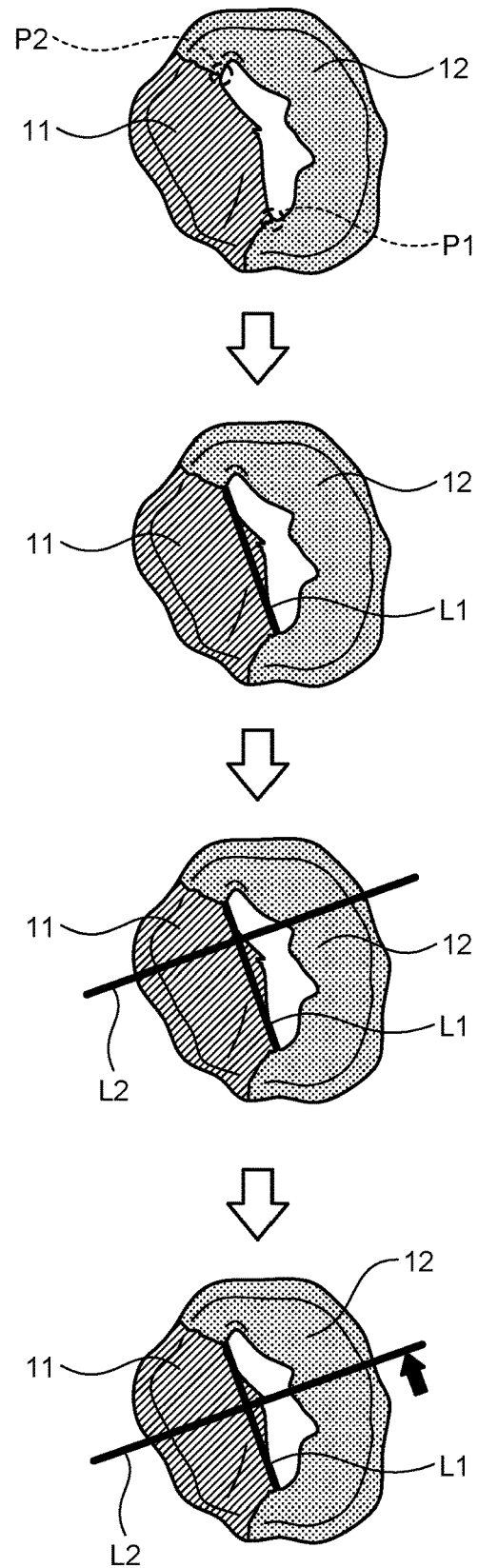
FIG. 4 is a drawing for explaining an example of a setting process performed by a setting function according to the first embodiment.

FIG. 4 is a drawing for explaining an example of the setting process performed by the setting function 354 according to the first embodiment. FIG. 4 illustrates an example in which, among the CT images at the time points t1 to t6 illustrated in FIG. 3, a cross-section is set with the mitral valve rendered in the CT image corresponding to the time point t1.

For example, at first, the setting function 354 identifies, as illustrated in the first section of FIG. 4, the anterior commissure P1 and the posterior commissure P2, which are feature positions of the mitral valve, from the CT image corresponding to the time point t1. The anterior commissure P1 and the posterior commissure P2 are sites connecting an anterior cusp 11 and a posterior cusp 12 to each other. In this situation, the process performed by the setting function 354 to identify the feature positions may be manually performed via the input interface 32 or may be performed on the basis of any of known image processing techniques. When the process is performed manually, the setting function 354 identifies positions designated via the input interface 32 as the feature positions (the anterior commissure P1 and the posterior commissure P2).

In contrast, when the process is performed by using any of known image processing techniques, the setting function 354 directly identifies the anterior commissure P1 and the posterior commissure P2 of the mitral valve rendered in the CT image corresponding to the time point t1 by using any of the known region segmentation techniques. Alternatively, the setting function 354 may segment the positions of the anterior cusp 11 and the posterior cusp 12 so as to identify the anterior commissure P1 and the posterior commissure P2 on the basis of the positions of the boundary therebetween.

In another example, by using a learning model that is constructed on the basis of training-purpose data prepared in advance with the use of a machine learning technique (which may be deep learning) and is configured to indicate the positions of the commissures, the setting function 354 may cause the learning model to output the positions of the anterior commissure P1 and the posterior commissure P2 by inputting the CT image corresponding to the time point t1 thereto. Further, in the example described above, the commissures are identified as the feature positions; however, possible embodiments are not limited to this example. For instance, the right fibrous trigone and the left fibrous trigone may be used.

When the feature positions have been identified as described above, the setting function 354 subsequently sets a cross-section on the basis of the identified positions. For example, as illustrated in the second section of FIG. 4, the setting function 354 sets a line segment L1 connecting the anterior commissure P1 to the posterior commissure P2. After that, as illustrated in the third section of FIG. 4, the setting function 354 sets a cross-section indicated by a line segment L2 orthogonal to the line segment L1.

In this situation, the position of the cross-section indicated by the line segment L2 may be set on the basis of any of various types of methods. For example, the setting function 354 obtains a condition related to the cross-section position that is set in advance and saved in the memory 34 or obtains a condition related to the cross-section position set by the user manually via the input interface 32. The condition related to the cross-section position may be set as a percentage or a numerical value indicating an absolute distance, on the basis of the distance from the anterior commissure to the posterior commissure, for example. Alternatively, the condition related to the cross-section position may be set as a percentage or a numerical value indicating an absolute distance, for example, on the basis of the distance from the middle point between the anterior commissure and the posterior commissure to either the anterior commissure or the posterior commissures.

Figure 5B:
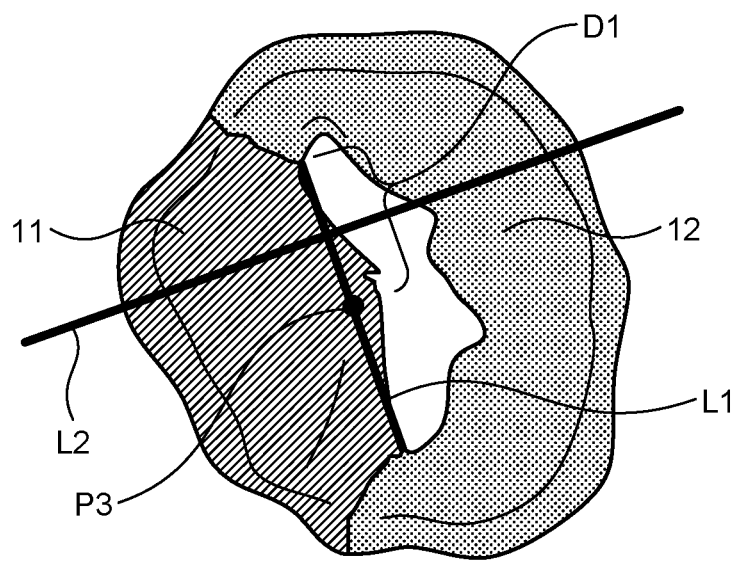
FIG. 5B is another drawing for explaining the example of the condition setting related to setting the cross-section position according to the first embodiment.

FIGS. 5A and 5B are drawings for explaining an example of the condition setting related to setting the cross-section position according to the first embodiment. FIG. 5A illustrates a GUI used in a situation where the user manually sets a condition via the input interface 32. For example, as illustrated in FIG. 5A, the controlling function 351 causes the display 33 to display a cross-section condition setting GUI including check boxes used for designating a range to set a numerical value "in the direction from the anterior commissure toward the posterior commissure", "in the direction from the middle point toward the posterior commissure", or "in the direction from the middle point toward the anterior commissure" and text boxes used for setting either an absolute distance or a percentage numerical value. In other words, the controlling function 351 causes an input screen to be displayed for receiving either the distance or the percentage numerical value that is set on the basis of the feature points of the plurality of tissues (the valve cusps of the mitral valve), as the condition of the cross-section position set with the plurality of tissues (the valve cusps of the mitral valve).

By using the GUI illustrated in FIG. 5A, the user sets a desirable condition. For example, via the input interface 32, the user checks the check box indicating "in the direction from the middle point toward the posterior commissure" and inputs "30" to the text box used for setting a percentage numerical value, as illustrated in FIG. 5A. Accordingly, a cross-section will be set in the position corresponding to "30% in the direction from the middle point toward the posterior commissure" on the line segment L1 connecting the anterior commissure to the posterior commissure. In other words, as illustrated in FIG. 5B, the setting function 354 sets the cross-section indicated by the line segment L2 in the position at "30%" in the direction from the middle point P3 toward the posterior commissure, while the distance D1 from the middle point of the line segment L1 to the posterior commissure is regarded as "1".

In the situation where the cross-section condition is set in advance and saved in the memory 34, the range to set a numerical value and the numerical value as described above are set in advance. The setting function 354 sets the cross-section indicated by the line segment L2 by reading the saved condition from the memory 34 and adopting the read condition.

Further, as illustrated in the fourth section of FIG. 4, it is also possible to manually set the cross-section indicated by the line segment L2, by using a mouse cursor or the like. In that situation, the controlling function 351 causes the line segment L2 indicating the cross-section position to be displayed on a display screen (so as to be superimposed on a clinical image). The user moves the line segment L2 to a desirable position via the input interface 32. The setting function 354 sets the cross-section in the position of the line segment L2 having been moved. Additionally, it is also possible to exercise control so as to restrict the range of positions in which the user is able to manually set a cross-section position on the basis of the anterior commissure and the posterior commissure. For example, the restriction may be imposed so that the user is able to move the line segment indicating the cross-section only perpendicularly to a line segment of which the end points are at the commissures or the user is unable to move the line segment indicating the cross-section beyond the commissures.

The cross-section setting process described above is merely an example. It is acceptable to use any method as long as the user is able to set a cross-section on which the user wishes to measure the measurement value. Further, in the above description, the example was explained in which the line segment of which the end points are at the commissures is set as a straight line; however, possible embodiments are not limited to this example. For instance, it is possible to set the line segment having a curved shape fitting the shape of the valve opening.

With respect to all the medical images in which the states were determined at step S102, the setting function 354 sets a cross-section as described above. FIG. 6 is a drawing illustrating an example of the cross-section setting process performed by the setting function 354 according to the first embodiment. For example, as illustrated in FIG. 6, the setting function 354 sets a cross-section indicated by a line segment L2 in each of the CT images at the time points t2 to t6, in addition to the CT image at the time point t1.

In this situation, with respect to the CT images at the time points t2 to t6, the setting function 354 may repeatedly perform the same process as the process performed on the CT image at the time point t1. Alternatively, the setting function 354 may set a cross-section in each of the CT images at the time points t2 to t6, by using the processing result from the CT image at the time point t1. In that situation, for example, the setting function 354 identifies correspondence relationships between the CT image at the time point t1 and the other CT images, by performing a position alignment between the CT image at the time point t1 set with the cross-section and each of the CT images at the other time points.

After that, the setting function 354 sets a cross-section in each of the CT images at the other time points on the basis of the identified correspondence relationships. For example, by using the positional correspondence relationship between the images based on the result of the position alignment performed between the CT image at the time point t1 and the CT image at the time point t2, the setting function 354 sets a cross-section in the CT image at the time point t2. Similarly, with respect to the CT images at the time points t3 to t6, the setting function 354 sets a cross-section by using each of the correspondence relationships with the CT image at the time point t1.

In this situation, it is possible to perform the position alignment by using any of known deformation position alignment techniques. Examples of the known deformation position alignment techniques include: a Free-Form Deformation (FFD) method and a Large Deformation Diffeomorphic Metric Mapping (LDDMM) method.

In the above description, the example was explained in which the cross-section is set in the direction perpendicular to the specific line segment (the line segment L1); however, possible embodiments are not limited to this example. It is also acceptable to allow the user to set a cross-section in an arbitrary direction.

The Structure-of-Interest Segmenting Process:

As explained at step S104 in FIG. 2, the segmenting function 355 segments the structures of interest from each of the plurality of medical images. More specifically, the segmenting function 355 obtains the structures of the plurality of tissues, from the medical images taken at a first time point and at a second time point different from the first time point, among the plurality of time points. More specifically, the segmenting function 355 obtains the structures of the plurality of tissues in the first state and the second state, from the medical image taken at the first time point at which the plurality of tissues are in a first state and taken at the second time point at which the plurality of tissues are in a second state different from the first state. For example, the segmenting function 355 segments structures of the mitral valve from the medical images taken of the mitral valve in the closed state and from the medical images taken of the mitral valve in the open state.

In this situation, the segmenting function 355 obtains the structure of each of the plurality of tissues rendered in each of the plurality of medical image taken in the first state and further obtains the structure of each of the plurality of tissues rendered in each of the plurality of medical images taken in the second state. For example, the segmenting function 355 obtains the structure of each of the valve leaflets of the heart valve rendered in the plurality of medical images in the first state, which is a state in which the heart valve is closed and further obtains the structure of each of the valve leaflets of the heart valve rendered in the plurality of medical images in the second state, which is a state in which the heart valve is open. In one example, the segmenting function 355 segments each of both of the anterior cusp and the posterior cusp of the mitral valve on the cross-section set in each of the CT images at the time points t1 to t6. In this situation, the structures of interest may be segmented by using the known region segmentation technique mentioned at step S102 (e.g., Otsu's binarization method based on CT values, a region growing method, a snake method, a graph cut method, or a mean shift method) or may be segmented by using a learning model for the structures of interest constructed on the basis of training-purpose data prepared in advance with the use of a machine learning technique (which may be deep learning). The process of calculating the length of the contact part:

As explained at step S105 in FIG. 2, the calculating function 356 calculates the measurement value related to the contact part between the plurality of tissues at the first time point, on the basis of the structures of the plurality of tissues at the second time point (the structures of interest at the second time point) and the structures of the plurality of tissues at the first time point (the structures of interest at the first time point) segmented by the segmenting function 355. More specifically, the calculating function 356 calculates the measurement value related to the contact part between the plurality of tissues in the first state, on the basis of the structures of the plurality of tissues in the second state (the structures of interest in the second state) and the structures of the plurality of tissues in the first state (the structures of interest in the first state).

For example, the calculating function 356 calculates the measurement value related to the contact part between the valve leaflets of the heart valve in the closed state, on the basis of the structure of the heart valve in the open state and the structure of the heart valve in the closed state. In one example, on the basis of the structures of the anterior cusp and the posterior cusp of the mitral valve in the open state and the structures of the anterior cusp and the posterior cusp of the mitral valve in the closed state, the calculating function 356 calculates the measurement value related to the contact part between the anterior cusp and the posterior cusp in the closed state. In other words, on the basis of a length related to the structures of the valve leaflets in the closed state (the first state) and a length related to the structures of the valve leaflets in the open state (the second state), the calculating function 356 calculates the measurement value related to the contact part of the heart valve in the closed state (the first state).

In this situation, the calculating function 356 is configured to select a first structure on the basis of features of the structures, from among the structures of the plurality of tissues segmented from each of the plurality of medical images taken in the first state (the structures of interest segmented from the medical images in the first state), to select a second structure on the basis of features of the structures, from among the structures of the plurality of tissues segmented from the medical images taken in the second state (the structures of interest segmented from the medical images in the second state), and to further calculate the measurement value related to the contact part between the plurality of tissues in the first state on the basis of the first structure and the second structure.

For example, the calculating function 356 is configured to calculate the length of the contact part of the heart valve, on the basis of: the length from a contact start point to the annulus of each of the valve leaflets of the heart valve rendered in the medical images in the closed state (the first state); and the length of each of the valve leaflets of the heart valve rendered in the medical images in the open state (the second state). In one example, the calculating function 356 calculates the length of the contact part of the heart valve, on the basis of: the shortest length from the contact start point to the annulus with respect to each of the valve leaflets of the heart valve rendered in the plurality of medical images in the closed state (the first state); and the longest length from the annulus to the valve tip end with respect to each of the valve leaflets of the heart valve rendered in the plurality of medical images in the open state (the second state).

For example, the calculating function 356 is configured to select the first structure in which the length from the contact start point to the annulus of the valve leaflet is the shortest with respect to each of the valve leaflets of the heart valve rendered in the plurality of medical images in the first state, to select the second structure in which the length from the annulus to the valve tip end is the longest with respect to each of the valve leaflets of the heart valve rendered in the plurality of medical images in the second state, to further calculate the difference between the first structure and the second structure with respect to each of the valve leaflets of the heart valve, and to obtain a measurement result being the smallest value among the calculated differences, as the length of the contact part of the heart valve.

In one example, the calculating function 356 performs the processes described below, while using the closed state of the heart valve as the first state and using the open state of the heart valve as the second state. For example, with respect to each of the anterior and the posterior cusps of the mitral valve, the calculating function 356 selects a structure in which the length from the start point of the contact part to the annulus is the shortest with respect to the mitral valve in the closed state, from among the CT images taken at the time points t2 to t5 of the mitral valve in the closed state. Further, with respect to the anterior and the posterior cusps of the mitral valve in the open state, the calculating function 356 selects a structure in which the length from the annulus to the valve tip end is the longest, from between the CT images taken at the time points t1 and t6 of the mitral valve in the open state. After that, with respect to each of the anterior and the posterior cusps, the calculating function 356 calculates the difference value between: the largest value among the lengths from the annulus to the valve tip end of the anterior cusp and the posterior cusp in the open state; and the smallest value among the lengths from the contact start point to the annulus of the anterior cusp and the posterior cusp in the closed state and further calculates the smaller of the difference values as the length of the contact part.

FIG. 7 is a drawing for explaining the calculating process performed by the calculating function 356 according to the first embodiment. FIG. 7 illustrates the cross-section (the cross-section indicated by the line segment L2 set with the mitral valve) set by the setting function 354. For example, the segmenting function 355 segments the anterior cusp 11 and the posterior cusp 12 illustrated in FIG. 7 from the cross-section set by the setting function 354, with respect to each of the CT images taken in the open state (the CT images at the time points t1 and t6) and the CT images taken in the closed state (the CT images at the time points t2 to t5) of the mitral valve.

The calculating function 356 calculates the lengths illustrated in FIG. 7 for each of the states of the mitral valve, with respect to the anterior cusp 11 and the posterior cusp 12 of the mitral valve segmented by the segmenting function 355. For example, with respect to the anterior cusp 11 and the posterior cusp 12 of the mitral valve at each of the time points t1 and t6, the calculating function 356 calculates a length "D2" from the annulus of the anterior cusp 11 to the tip end of the anterior cusp 11 in the open state, as well as a length "D3" from the annulus of the posterior cusp 12 to the tip end of the posterior cusp 12. In this situation, the length "D2" from the annulus of the anterior cusp 11 to the tip end of the anterior cusp 11 in the open state and the length "D3" from the annulus of the posterior cusp 12 to the tip end of the posterior cusp 12 are each the length of the curve fitted along the shape of the valve cusp.

Further, for example, with respect to the anterior cusp 11 and the posterior cusp 12 of the mitral valve at each of the time points t2 to t5, the calculating function 356 calculates a length "D4" from the start point of the contact part between the anterior cusp 11 and the posterior cusp 12 to the annulus of the anterior cusp 11 in the closed state, as well as a length "D5" from the start point of the contact part to the annulus of the posterior cusp 12. The start point of the contact part denotes the position in which the contact starts from the annulus toward the tip end of each of the valve cusps. Further, the length "D4" and the length "D5" are each the length of the curve fitted along the shape of the valve cusp.

When having calculated the lengths of the valve cusps at each of the time points in each of the states as described above, the calculating function 356 selects a representative value in each of the states on the basis of an arbitrary condition. For example, from among the lengths of each of the valve cusps of the mitral valve in the open state, the calculating function 356 determines a representative value. In this situation, the condition used for selecting the representative value in the open state may state, for example, that "the largest value is to be adopted as the representative value".

In principle, the length from the annulus of the anterior cusp or the posterior cusp to the tip end of the anterior cusp or the posterior cusp does not change in a short period of time (e.g., one cycle of the cardiac phase). However, because the tip ends of a valve in the open state move frequently, the temporal resolution of an X-ray CT apparatus is not sufficient to properly render the tip end part. Accordingly, in some situations, mutually-different values may be calculated at mutually-different time points, as the length from the annulus of the anterior cusp or the posterior cusp to the tip end of the anterior cusp or the posterior cusp. Consequently, there is a possibility that the lengths from the annuli of the anterior and the posterior cusps to the tip ends of the anterior and the posterior cusps may be calculated more accurately, by adopting the largest value among the measurement values from the plurality of CT images as the representative value.

For this reason, for example, the calculating function 356 compares and selects the largest value between the length "D2" values at the time points (t1 and t6) in the open state, on the basis of the abovementioned condition. In other words, the calculating function 356 compares the length "D2" at t1 with the length "D2" at t6 and selects the largest value as the representative value for the length from the annulus of the anterior cusp 11 to the tip end of the anterior cusp 11 in the open state. Similarly, the calculating function 356 compares the length "D3" at t1 with the length "D3" at t6 and selects the largest value as the representative value for the length from the annulus of the posterior cusp 12 to the tip end of the posterior cusp 12 in the open state.

In this situation, the condition used for determining the representative value in the open state does not necessarily have to be the condition described above (i.e., the largest value), and it is acceptable to use a condition indicating that, for example, "an average value is to be adopted as a representative value". Similarly, because the tip ends of a valve in the open state move frequently, mutually-different values may be calculated at mutually-different time points in some situations, as the length from the annulus of the anterior cusp or the posterior cusp to the tip end of the anterior cusp or the posterior cusp, especially for patients suffering from mitral insufficiency. Consequently, there is a possibility that the lengths from the annuli of the anterior and the posterior cusp to the tip ends of the anterior and the posterior cusp may be calculated more accurately, by adopting an average value of the measurement values from the plurality of images as the representative value.

Further, for example, with respect to each of the lengths from the start point of the contact part to the annulus of the anterior cusp and to the annulus of the posterior cusp of the mitral valve in the closed state, the calculating function 356 determines a representative value. In this situation, the condition used for selecting the representative value in the closed state may state, for example, that "the smallest value is to be adopted as the representative value".

As explained above, in principle, the lengths of the anterior cusp and the posterior cusp do not change in a short period of time. Accordingly, when the length from the annulus part of each of the anterior and the posterior cusps to the start point of the contact part is the smallest, it is expected that the length from the start point of the contact part to the tip end of each of the valve cusps is the largest. Thus, there is a high possibility that the length of the contact part is in the state of being longer.

For this reason, for example, the calculating function 356 selects the smallest value among the length "D4" values at the time points in the closed state (t2 to t5), on the basis of the abovementioned condition. In other words, the calculating function 356 compares the length "D4" at t2, the length "D4" at t3, the length "D4" at t4, and the length "D4" at t5 and selects the smallest value as the representative value for the length from the annulus part of the anterior cusp 11 to the start point of the contact part in the closed state. Similarly, the calculating function 356 compares the length "D5" at t2, the length "D5" at t3, the length "D5" at t4, and the length "D5" at t5 and selects the smallest value as the representative value for the length from the annulus part of the posterior cusp 12 to the start point of the contact part in the closed state.

In this situation, the condition used for determining the representative value in the closed state does not necessarily have to be the condition described above (i.e., the smallest value), and it is acceptable to use a condition indicating that, for example, "an average value is to be adopted as a representative value". As explained above, when the length from the annulus part of each of the anterior and the posterior cusps to the start point of the contact part is the smallest, there is a high possibility that the length of the contact part is in the state of being longer; however, that may not necessarily be true. Further, as explained above, when the smallest value among the length "D4" values and the smallest value among the length "D5" values are each independently selected, there is a possibility that the length "D4+D5" may not be long enough to reach the diameter of the mitral valve, in the situation where the position of the contact part is shifted toward the respective valve cusp side.

In view of the circumstances described above, for example, the calculating function 356 calculates an average value of the length "D4" values at the time points in the closed state (t2 to t5) on the basis of the condition indicating that "an average value is to be adopted as the representative value". In other words, the calculating function 356 calculates an average of the length "D4" at t2, the length "D4" at t3, the length "D4" at t4, and the length "D4" at t5 and further selects the average value as the representative value for the length from the annulus part of the anterior cusp 11 to the start point of the contact part in the closed state. Similarly, the calculating function 356 calculates an average of the length "D5" at t2, the length "D5" at t3, the length "D5" at t4, and the length "D5" at t5 and further selects the average value as the representative value for the length from the annulus part of the posterior cusp 12 to the start point of the contact part in the closed state.

Further, in the above description, the example was explained in which the representative value is selected on the basis of the condition, with respect to the anterior cusp 11 and with respect to the posterior cusp 12. However, the calculating function 356 may be configured to select a representative value on the basis of the condition with respect to one of the valve cusps between the anterior cusp 11 and the posterior cusp 12, so as to obtain a representative value of the other valve cusp from a medical image corresponding to the selected representative value.

More specifically, the calculating function 356 may select, from within a first medical image among the plurality of medical images, the length from the contact start point to the annulus of a first valve leaflet among the valve leaflets of the heart valve in the closed state (the first state) and may obtain, from within the first medical image, the length from the contact start point to the annulus of a second valve leaflet different from the first valve leaflet. In one example, the calculating function 356 compares the length "D4" values at the time points in the closed state (t2 to t5) with one another, so as to select the smallest value. In this situation, let us discuss an example in which the length "D4" at t3 is the smallest and is selected as the representative value for the length from the annulus part of the anterior cusp 11 to the start point of the contact part. In this example, the calculating function 356 selects the length "D5" at t3 as the representative value for the length from the annulus part of the posterior cusp 12 to the start point of the contact part.

Further, at the time of calculating the representative values in the open state and the closed state as described above, it is also acceptable to identify outliers by using a statistical method (e.g., Smirnov Grubbs test) and to exercise control so as not to use the outliers as the representative value (e.g., the largest value, the smallest value, or the average value).

As explained above, the calculating function 356 is configured to determine the representative value in each of the states on the basis of the arbitrary conditions. In relation to this, the abovementioned conditions may be set in advance or may be set by the user via the input interface 32. FIG. 8 is a drawing for explaining an example of condition settings related to determining the representative values according to the first embodiment. FIG. 8 illustrates a GUI used when the user manually sets the condition via the input interface 32.

For example, as illustrated in FIG. 8, the controlling function 351 causes the display 33 to display the GUI including the checkboxes "Largest", "Smallest", and "Average" used for an "Open state representative value condition setting" and the checkboxes "Largest", "Smallest", and "Average" used for a "Closed state representative value condition setting". In this situation, as illustrated in FIG. 8, the controlling function 351 may display a GUI further including a checkbox used for setting whether or not the outliers are to be excluded. In other words, the controlling function 351 causes an input screen to be displayed so as to be used for selecting a representative value of the structures of the plurality of tissues (the structures of the valve cusps of the mitral valve) segmented from each of the plurality of medical images taken in the closed state (the first state) and a representative value of the structures of the plurality of tissues (the structures of the valve cusps of the mitral valve) segmented from each of the plurality of medical images taken in the open state (the second state).

The user sets a desirable condition by using the GUI illustrated in FIG. 8. For example, via the input interface 32, as illustrated in FIG. 8, the user checks the checkbox "Exclude outliers", checks the checkbox "Largest" for the "Open state representative value condition setting", and checks the checkbox "Smallest" for the "Closed state representative value condition setting". As a result, the conditions can set so as to select the largest value as the representative value in the open state and to select the smallest value as the representative value in the closed state, while the outliers are excluded.

When the conditions of the representative values are set in advance and saved in the memory 34, the calculating function 356 determines the representative values in the open state and the closed state by reading the saved conditions from the memory 34 and adopting the read conditions.

Further, when there is only one image belonging to the open state or the closed state, it is also acceptable to skip the abovementioned comparing process and to adopt the measurement value from the image.

When having determined the representative values in each of the states as described above, the calculating function 356 calculates the length of the contact part between the anterior cusp and the posterior cusp, from the representative value in the open state and the representative value in the closed state. For example, with respect to the anterior cusp 11 and with respect to the posterior cusp 12, the calculating function 356 calculates the value of the difference between the representative value in the open state and the representative value in the closed state. In other words, with respect to the anterior cusp 11 and with respect to the posterior cusp 12, the calculating function 356 is able to calculate the length from the start point of the contact part to the tip end of the valve.

Figure 9:
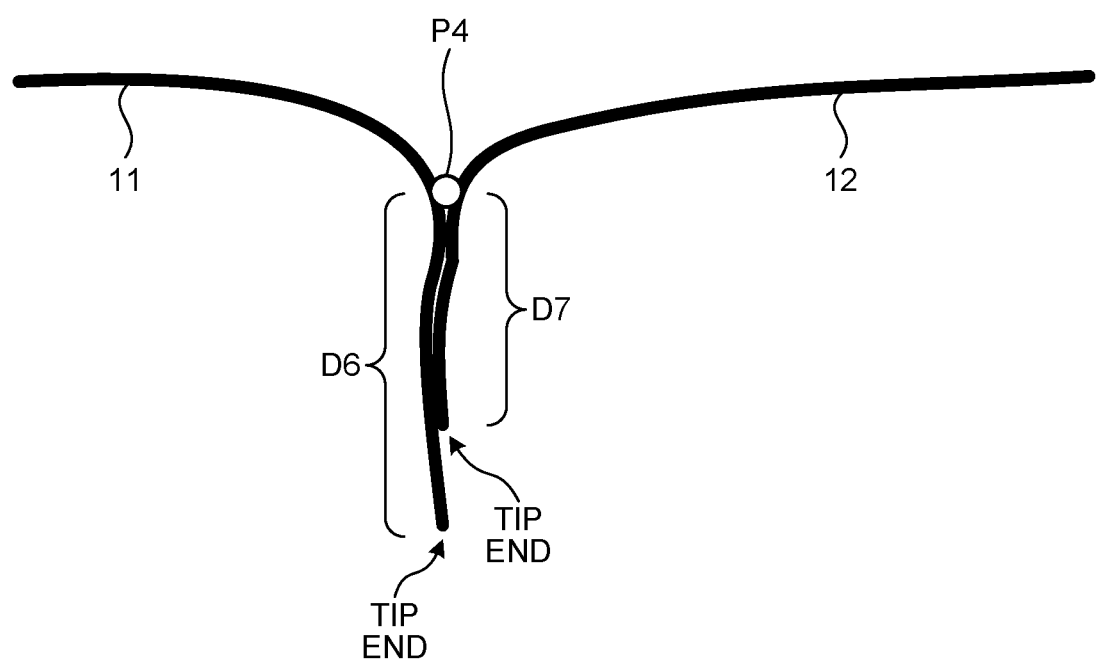
FIG. 9 is a drawing for explaining a calculating process performed by the calculating function according to the first embodiment.

FIG. 9 is a drawing for explaining the calculating process performed by the calculating function 356 according to the first embodiment. FIG. 9 illustrates the cross-section set by the setting function 354 (the cross-section indicated by the line segment L2 set with the mitral valve). For example, by subtracting the representative value for the length "D4" in the closed state from the representative value for the length "D2" in the open state, the calculating function 356 calculates "D6: the length from the start point P4 of the contact part to the tip end of the anterior cusp 11" illustrated in FIG. 9. Similarly, by subtracting the representative value for the length "D5" in the closed state from the representative value for the length "D3" in the open state, the calculating function 356 calculates "D7: the length from the start point P4 of the contact part to the tip end of the posterior cusp 12" illustrated in FIG. 9.

After that, the calculating function 356 compares the length "D6" from the start point P4 of the contact part to the tip end of the anterior cusp 11, with the length "D7" from the start point P4 of the contact part to the tip end of the posterior cusp 12 and further calculates the shorter of the two (i.e., the length "D7") as the length (called "coaptation height") of the contact part between the anterior cusp 11 and the posterior cusp 12. In this manner, the calculating function 356 is able to calculate the length of the contact part between the anterior cusp 11 and the posterior cusp 12 by using the lengths of the valve cusps and the length from the annulus to the start point of the contact part of each of the valve cusps.

The Measurement Value Display Process:

As explained at step S106 in FIG. 2, when the calculating function 356 has calculated the measurement values, the controlling function 351 is configured to exercise control so as to cause the display 33 to display the measurement values. For example, the controlling function 351 causes the length of the contact part calculated by the calculating function 356 to be displayed while being superimposed on a clinical image, to be displayed in a region different from that of a clinical image, or to be displayed together with a schematic drawing of a cross-section of the mitral valve.

FIRST MODIFICATION EXAMPLE

In the embodiment described above, the example was explained in which the setting function 354 sets the single cross-section on which the length of the contact part is to be measured; however, possible embodiments are not limited to this example. It is also acceptable to set a plurality of cross-sections, so as to calculate the length of the contact part on each of the cross-sections. In that situation, the setting function 354 may set the plurality of cross-sections by repeatedly performing the process of identifying feature points of the plurality of tissues (e.g., the commissures of the mitral valve) and the process of setting a cross-section on the basis of the identified feature points.

In another example, the setting function 354 may set a plurality of cross-sections perpendicular to a line segment (e.g., the line segment L1) of which the end points are at the feature points of the plurality of tissues (e.g., the commissures of the mitral valve), the cross-sections being positioned at arbitrary intervals between one end point to the other end point of the line segment. The arbitrary intervals may be set in advance or may be set by the user while using a GUI (not illustrated). Further, the arbitrary intervals may be regular intervals or irregular intervals.

Figures 10A, 10B:
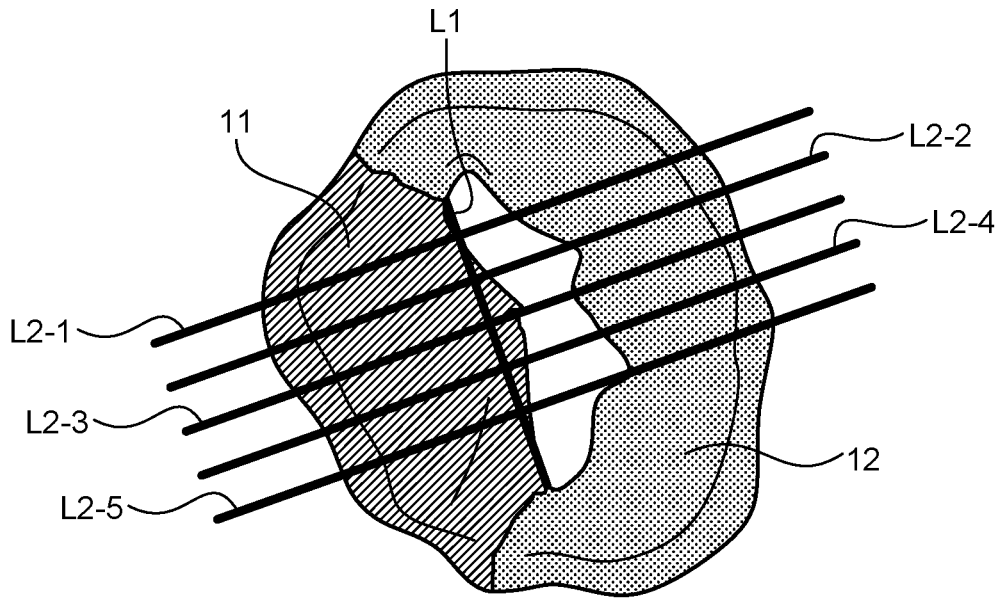
FIG. 10A is a drawing illustrating an example of a setting process performed by a setting function according to a first modification example.
FIG. 10B is a drawing illustrating an example of a display process performed by a controlling function according to the first modification example.

FIG. 10A is a drawing illustrating an example of the setting process performed by the setting function 354 according to a first modification example. For instance, as illustrated in FIG. 10A, the setting function 354 sets line segments L2-1 to L2-5 that are orthogonal to the line segment L1 set on the basis of the commissures of the mitral valve. The length of the contact part on each of the cross-sections indicated by the line segments L2-1 to L2-5 is calculated by repeatedly performing steps S104 through S106 explained above.

When the lengths of the contact part have been calculated on the plurality of cross-sections as explained above, the controlling function 351 causes the calculated lengths of the contact part to be displayed in any of various types of methods. FIG. 10B is a drawing illustrating an example of the display process performed by the controlling function 351 according to the first modification example. For instance, as illustrated in FIG. 10B, the controlling function 351 is able to cause display information to be displayed so that the lengths on the plurality of cross-sections (L2-1 to L2-5) are arranged in a list.

In one example, as illustrated in FIG. 10B, the controlling function 351 is able to cause the display information to be displayed to indicate, with respect to each of the cross-section positions, representative values of the anterior cusp in the open state and the closed state, representative values of the posterior cusp in the open state and the closed state, and the length of the contact part. Further, as illustrated in FIG. 10B, the controlling function 351 is able to cause the display information to be displayed, while including average values and total values of the representative values. Further, it is also acceptable to display information about descriptive statistics (an average value, the largest value, the smallest value, or a variance) or inferential statistics (e.g., a confidence interval) of the information about the lengths of the contact part on the plurality of cross-sections. Furthermore, the controlling function 351 may cause the various types of information about the lengths illustrated in FIG. 10B to be displayed while being positioned side by side with, or superimposed on, a schematic drawing or clinical information.

Figure 11:
FIG. 11 is a drawing illustrating another example of the display process performed by the controlling function according to the first modification example.

In another example, the controlling function 351 may cause a graph to be displayed, to indicate a relationship between information about the cross-section positions (e.g., distances from a commissure) and the lengths of the contact part. FIG. 11 is a drawing illustrating the example of the display process performed by the controlling function 351 according to the first modification example. For example, as illustrated in FIG. 11, the controlling function 351 displays a curve L3 indicating the length of the contact part with respect to each of different distances from the anterior commissure of the mitral valve. In that situation, at first, the setting function 354 sets the plurality of cross-sections on the line segment L1 connecting the anterior commissure to the posterior commissure, so that the calculating function 356 calculates the length of the contact part on each of the cross-sections. After that, the controlling function 351 generates and displays a graph depicting the curve L3, on the basis of the length of the contact part with respect to each of the cross-section positions calculated by the calculating function 356.

Figure 12:
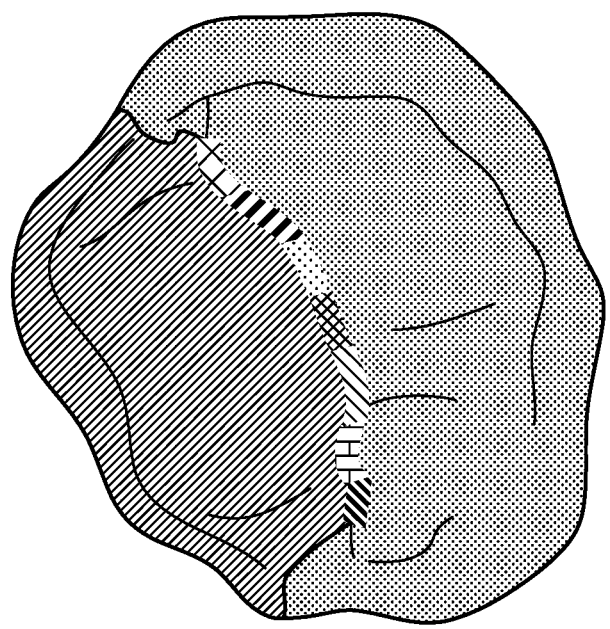
FIG. 12 is a drawing illustrating yet another example of the display process performed by the controlling function according to the first modification example.

In yet another example, other than the abovementioned graph, the controlling function 351 may cause a display image to be displayed so that information based on the measurement values with respect to each of the plurality of cross-section positions is indicated in a medical image. FIG. 12 is a drawing illustrating the example of the display process performed by the controlling function 351 according to the first modification example. For example, as illustrated in FIG. 12, the controlling function 351 displays a display image in which, in a medical image of the mitral valve, color information assigned according to the lengths of the contact part is superimposed in correspondence with the positions of the contact part and the lengths of the contact part in these positions. This configuration makes it possible to understand, at a glance, the correspondence relationship between the positions of the contact part and the lengths of the contact part in these positions.

Figure 13:
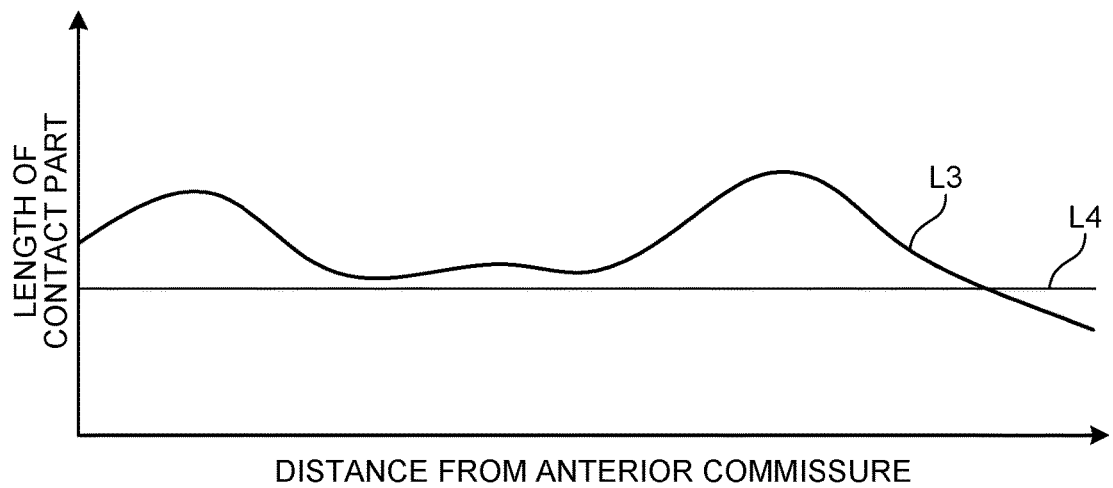
FIG. 13 is a drawing illustrating yet another example of the display process performed by the controlling function according to the first modification example.

In yet another example, the controlling function 351 may exercise control so as to display, with an emphasis, values in a range set in advance (e.g., abnormal values, characteristic values, or values within a range to which a treatment clip for the heart valve can be applied), among the measurement values such as the length of the contact part on each of the cross-sections. For example, the controlling function 351 causes display information to be displayed over a graph indicating the measurement values respectively corresponding to the plurality of cross-section positions, the display information indicating a threshold value used for judging the measurement values. FIG. 13 is a drawing illustrating the example of the display process performed by the controlling function 351 according to the first modification example. For example, as illustrated in FIG. 13, the controlling function 351 displays, over a graph, a straight line L4 indicating a threshold value for the length of the contact part used for judging abnormal values and characteristic values. With this arrangement, for example, the user is able to easily recognize the positions (the part where the length of the contact part is below the straight line L4 in the graph) in the mitral valve where the treatment clip for the heart valve cannot be placed.

For example, a treatment clip for the mitral valve may be placed for a patient suffering from mitral insufficiency by which the mitral valve does not fully close and allows the blood to flow backward into the left atrium. By clipping together the anterior cusp and the posterior cusp of the mitral valve with the use of the treatment clip, the backward blood flow is decreased. In this situation, during manipulations of placing treatment clips, the position of a temporarily-placed treatment clip may be corrected or an additional treatment clip may be placed, in accordance with the status of the backward blood flow. In the process of placing a treatment clip, the medical information processing apparatus 3 is able to assist the placement of the treatment clip in an appropriate position, by presenting an applicable range for the treatment clip in the valve cusps and helping understanding the position where the placement of the treatment clip is possible.

SECOND MODIFICATION EXAMPLE

In the above description, the example was explained in which the processes are performed at steps 5102 through 5106 on all the obtained images; however, possible embodiments are not limited to this example. For instance, it is also acceptable to exercise control so that the processes will not be performed on certain images that do not satisfy a predetermined criterion. In other words, at least one of the judging function 353, the setting function 354, the segmenting function 355, and the calculating function 356 may be configured to judge image quality of the medical images so that the processes will be performed on certain medical images of which the image quality exceeds a predetermined state. For example, at step 5102, the judging function 353 performs the process of judging the image quality of the images, and when there are one or more images of which the image quality is equal to or lower than a certain level, control is exercised so that the images having low image quality will not be utilized in the processes at the subsequent stages. In an example, control may be exercised so that, when the user designates one or more images having many artifacts, the processes will not be performed on those images. Alternatively, control may be exercised later so that the measurement values from those images will not be used.

THIRD MODIFICATION EXAMPLE

In the description above, the example was explained in which, at step S103, the control is exercised so as to use the cross-sections defined by the predetermined condition or designated by the user, as the cross-section positions in which the measurement values are calculated; however, possible embodiments are not limited to this example. For instance, a cross-section may be set by using information about a tissue of interest obtained from another modality.

In one example, the setting function 354 may be configured to identify a position having mitral insufficiency (where a backward flow is present) from an ultrasound image taken of the same patient and to further set a cross-section corresponding to the position as a cross-section on which the measurement values are to be calculated. In that situation, the setting function 354 is configured to segment a feature position (e.g., the mitral valve or a commissure) from the ultrasound image and to perform a position alignment with a corresponding feature position in a CT image, so as to identify the position in the mitral valve having the insufficiency from the CT image. In this situation, it is possible to perform the position alignment by using any of known deformation position alignment techniques.

FOURTH MODIFICATION EXAMPLE

In the description above, the example was explained in which the structures of interest (the anterior cusp and the posterior cusp of the mitral valve) are segmented on the cross-sections set at step S103 so as to calculate the measurement values; however, possible embodiments are not limited to this example. For instance, at certain time points after step S101 and before step S103, the structures of interest (the anterior cusp and the posterior cusp of the mitral valve) in an image may be segmented in advance from the entire image. In this manner, when the structures of interest are segmented in advance from the entire image before setting the cross-sections at step S103, it is possible to finish the structure-of-interest segmenting process in the single session at the beginning, even when the measurement values related to the contact part are calculated by setting a plurality of cross-sections.

FIFTH MODIFICATION EXAMPLE

In the above description, the example was explained in which, at step S104, the length of the contact part is calculated, by calculating the length from each of the annulus parts of the anterior and the posterior cusps to the start point of the contact part in the closed state; however, possible embodiments are not limited to this example. It is also acceptable to calculate a value other than the length of the contact part, as a measurement value related to the contact part. In one example, to calculate the length of a part that can be clipped by a treatment clip for the heart valve, it is also acceptable to use, as a length in the closed state, the length from each of the annulus parts of the anterior and the posterior cusps to a position having the largest curvature.

In that situation, the calculating function 356 calculates the length related to the contact part of the heart valve, on the basis of: the length from the point having the largest curvature to the annulus with respect to each of the valve leaflets of the heart valve rendered in the medical images in the closed state (the first state); and the length from the annulus to the valve tip end with respect to each of the valve leaflets of the heart valve rendered in the medical images in the open state (the second state). For example, the calculating function 356 calculates a length over which a manipulation on the heart valve is possible, on the basis of: the shortest length from the point having the largest curvature to the annulus with respect to each of the valve leaflets of the heart valve rendered in the plurality of medical images in the closed state (the first state); and the longest length from the annulus to the valve tip end with respect to each of the valve leaflets of the heart valve rendered in the plurality of medical images in the open state (the second state).

In one example, the calculating function 356 selects a first structure in which the length from the point having the largest curvature of the valve leaflet to the annulus is the shortest, with respect to each of the valve leaflets of the heart valve rendered in the plurality of medical images in the first state, further selects a second structure in which the length is the longest, with respect to each of the valve leaflets of the heart valve rendered in the plurality of medical images in the second state, calculates the difference between the first structure and the second structure with respect to each of the valve leaflets of the heart valve, and obtains a measurement result being the smallest value among the calculated differences, as the length over which the manipulation on the heart valve is possible.

Figure 14:
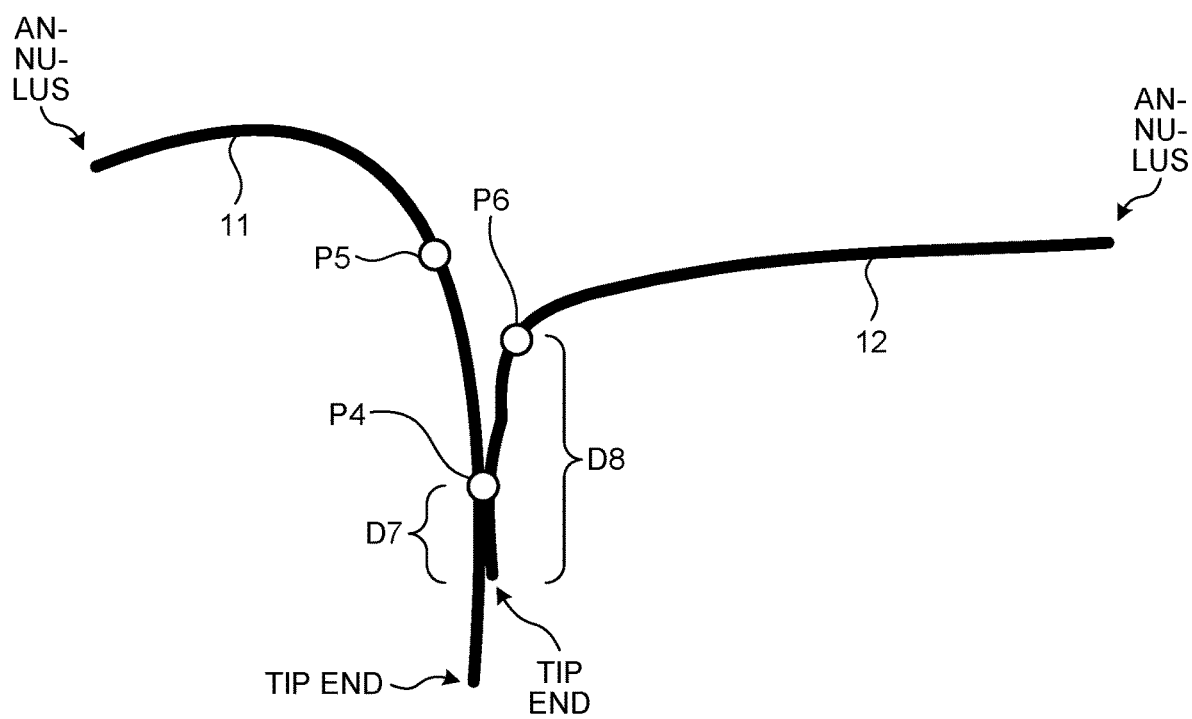
FIG. 14 is a drawing for explaining an example of a calculating process performed by a calculating function according to a fifth modification example.

FIG. 14 is a drawing for explaining an example of the calculating process performed by the calculating function 356 according to a fifth modification example. FIG. 14 illustrates a cross-section set by the setting function 354 (the cross-section indicated by the line segment L2 set with the mitral valve). For example, with respect to the anterior cusp 11 in the closed state, the calculating function 356 calculates the length from the annulus to a position P5 in which the curvature is the largest. Similarly, with respect to the posterior cusp 12 in the closed state, the calculating function 356 calculates the length from the annulus to a position P6 in which the curvature is the largest. After that, the calculating function 356 determines a representative value of the anterior cusp 11 in the closed state and a representative value of the posterior cusp 12 in the closed state.

Subsequently, the calculating function 356 calculates the "length from the position P5 in which the curvature is the largest to the tip end, with respect to the anterior cusp 11" illustrated in FIG. 14, by subtracting the representative value of the anterior cusp 11 in the closed state, from the representative value among the length "D2" values of the anterior cusp 11 in the open state. Similarly, the calculating function 356 calculates the "length from the position P6 in which the curvature is the largest to the tip end, with respect to the posterior cusp 12" illustrated in FIG. 14, by subtracting the representative value of the posterior cusp 12 in the closed state, from the representative value among the length "D3" values of the posterior cusp 12 in the open state.

After that, the calculating function 356 compares the "length from the position P5 in which the curvature is the largest to the tip end, with respect to the anterior cusp 11" with the "length from the position P6 in which the curvature is the largest to the tip end, with respect to the posterior cusp 12" and calculates the shorter of the two as the length of a section that can be clipped by a treatment clip for the heart valve. In other words, the calculating function 356 calculates the length "D8" illustrated in FIG. 14 as the length of the section that can be clipped by the treatment clip for the heart valve.

In the present embodiment, the example was based on the premise that the plurality of structures are in contact with each other without exception; however, for patients suffering from mitral insufficiency or the like, the plurality of structures (the anterior cusp and the posterior cusp) may not be in contact with each other in some situations. Even in those situations, it is possible to calculate the length of the section that can be clipped by the treatment clip for the heart valve, by determining the measurement value in the closed state as the length from each of the annulus parts of the anterior and the posterior cusps to the position in which the curvature is the largest. In this situation, the abovementioned method for calculating the length of the clippable section on the basis of the curvature is merely an example. It is acceptable to use any other method as long as it is possible to estimate the range (the distance) in which the plurality of structures can be in contact with each other by making a conjecture from geometric information of the plurality of structures.

As explained above, according to the first embodiment, the image obtaining function 352 is configured to obtain the medical images taken at the plurality of time points. The segmenting function 355 is configured to obtain the structures of the plurality of tissues from the medical images taken at the first time point and at the second time point different from the first time point, among the plurality of time points. The calculating function 356 is configured to calculate the measurement values related to the contact part between the plurality of tissues at the first time point, on the basis of the structures of the plurality of tissues at the second time point and the structures of the plurality of tissues at the first time point obtained by the segmenting function 355. Accordingly, the medical information processing apparatus 3 according to the first embodiment is able to calculate the measurement values related to the contact part on the basis of the structures of the plurality of tissues at the plurality of time points and thus makes it possible to accurately perform the measuring process relevant to the contact part.

Further, according to the first embodiment, the segmenting function 355 is configured to obtain the structures of the plurality of tissues in the first state and in the second state, from the medical images taken at the first time point at which the plurality of tissues are in the first state and taken at the second time point at which the plurality of tissues are in the second state different from the first state, respectively. The calculating function 356 is configured to calculate the measurement values related to the contact part between the plurality of tissues in the first state, on the basis of the structures of the plurality of tissues in the second state and the structures of the plurality of tissues in the first state. Consequently, the medical information processing apparatus 3 according to the first embodiment is able to calculate the measurement values related to the contact part, on the basis of the structures at the time points at which the plurality of tissues are in the mutually-different states and thus makes it possible to more accurately perform the measuring process relevant to the contact part.

Further, according to the first embodiment, the segmenting function 355 is configured to obtain each of the structures of the plurality of tissues rendered in each of the plurality of medical images taken in the first state and to obtain each of the structures of the plurality of tissues rendered in each of the plurality of medical images taken in the second state. From among the structures of the plurality of tissues segmented from each of the plurality of medical images taken in the first state, the calculating function 356 is configured to select the first structure on the basis of the features of the structures. From among the structures of the plurality of tissues segmented from the plurality of medical images taken in the second state, the calculating function 356 is configured to select the second structure on the basis of the features of the structures. Further, the calculating function 356 is configured to calculate the measurement values related to the contact part between the plurality of tissues in the first state, on the basis of the first structure and the second structure. Consequently, the medical information processing apparatus 3 according to the first embodiment is able to determine the representative value from each of the plurality of medical images taken in the mutually-different states and to thus makes it possible to more accurately perform the measuring process relevant to the contact part.

Further, according to the first embodiment, the plurality of tissues are the valve leaflets of the heart valve. The segmenting function 355 is configured to obtain the structures of the valve leaflets of the heart valve rendered in the medical images in the first state, which is the state in which the heart valve is closed and to obtain the structures of the valve leaflets of the heart valve rendered in the medical images in the second state, which is the state in which the heart valve is open. The calculating function 356 is configured to calculate the measurement values related to the contact part of the heart valve in the first state, on the basis of the length related to the structures of the valve leaflets in the first state and the length related to the structures of the valve leaflets in the second state. Consequently, the medical information processing apparatus 3 according to the first embodiment makes it possible to calculate the measurement values related to the contact part of the heart valve from the lengths related to the structures of the valve leaflets in the mutually-different states.

Further, according to the first embodiment, the calculating function 356 is configured to calculate the length of the contact part of the heart valve, on the basis of: the length from the contact start point to the annulus with respect to each of the valve leaflets of the heart valve rendered in the medical images in the first state and the length from the annulus to the valve tip end with respect to each of the valve leaflets of the heart valve rendered in the medical images in the second state. Consequently, the medical information processing apparatus 3 according to the first embodiment is able to calculate the length of the contact part of the heart valve by using the values that can easily be rendered in the medical images and can easily be measured and thus makes it possible to more accurately measure the contact part.

Further, according to the first embodiment, the segmenting function 355 is configured to obtain the structures of the valve leaflets of the heart valve rendered in the plurality of medical images in the first state and to obtain the structures of the valve leaflets of the heart valve rendered in the plurality of medical images in the second state. The calculating function 356 is configured to select, from within the first medical image among the plurality of medical images, the length from the contact start point to the annulus with respect to the first valve leaflet among the valve leaflets of the heart valve in the first state and to further obtain the length from the contact start point to the annulus with respect to the second valve leaflet different from the first valve leaflet from the first medical image, so as to calculate the length of the contact part of the heart valve, on the basis of: the length from the contact start point to the annulus of the first valve leaflet; the length from the contact start point to the annulus of the second valve leaflet; and the length from the annuls to the valve tip end of the first valve leaflet and the length from the annulus to the valve tip end of the second valve leaflet selected from within the plurality of medical images in the second state. Consequently, the medical information processing apparatus 3 according to the first embodiment makes it possible to select the representative values conforming to the closed state of the heart valve.

Further, according to the first embodiment, the segmenting function 355 is configured to obtain the structures of the valve leaflets of the heart valve rendered in the plurality of medical images in the first state and to obtain the structures of the valve leaflets of the heart valve rendered in the plurality of medical images in the second state. The calculating function 356 is configured to calculate the length of the contact part of the heart valve, on the basis of: the shortest length from the contact start point to the annulus with respect to each of the valve leaflets of the heart valve rendered in the plurality of medical images in the first state; and the longest length from the annulus to the valve tip end with respect to each of the valve leaflets of the heart valve rendered in the plurality of medical images in the second state. Consequently, the medical information processing apparatus 3 according to the first embodiment makes it possible to calculate the contact part of the heart valve, by using the values that are more approximate to the actual values.

Further, according to the first embodiment, the calculating function 356 is configured to select the first structure in which the length from the contact start point to the annulus of the valve leaflet is the shortest with respect to each of the valve leaflets of the heart valve rendered in the plurality of medical images in the first state, to select the second structure in which the length is the longest with respect to each of the valve leaflets of the heart valve rendered in the plurality of medical images in the second state, to calculate the difference between the first structure and the second structure with respect to each of the valve leaflets of the heart valve, and to obtain the measurement result being the smallest value among the calculated differences, as the length of the contact part of the heart valve. Consequently, the medical information processing apparatus 3 according to the first embodiment makes it possible to more accurately measure the length of the contact part of the heart valve.

Further, according to the first embodiment, the calculating function 356 is configured to calculate the length related to the contact part of the heart valve, on the basis of: the length from the point having the largest curvature to the annulus with respect to each of the valve leaflets of the heart valve rendered in the medical images in the first state; and the length from the annuls to the valve tip end with respect to each of the valve leaflets of the heart valve rendered in the medical images in the second state. Consequently, the medical information processing apparatus 3 according to the first embodiment is able to calculate the length related to the contact part of the heart valve, by using the values that can easily be rendered in the medical images and can easily be measured and thus makes it possible to more accurately perform the measuring process related to the contact part.

Further, according to the first embodiment, the segmenting function 355 is configured to obtain the structures of the valve leaflets of the heart valve rendered in the plurality of medical images in the first state and to obtain the structures of the valve leaflets of the heart valve rendered in the plurality of medical images in the second state. The calculating function 356 is configured to calculate the length over which a manipulation on the heart valve is possible, on the basis of: the shortest length from the point having the largest curvature to the annulus with respect to each of the valve leaflets of the heart valve rendered in the plurality of medical images in the first state; and the longest length from the annulus to the valve tip end with respect to each of the valve leaflets of the heart valve rendered in the plurality of medical images in the second state. Consequently, the medical information processing apparatus 3 according to the first embodiment makes it possible to calculate the length over which the manipulation on the heart valve is possible, by using the values that are more approximate to the actual values.

Further, according to the first embodiment, the calculating function 356 is configured to select the first structure in which the length from the point having the largest curvature of the valve leaflet to the annulus is the shortest with respect to each of the valve leaflets of the heart valve rendered in the plurality of medical images in the first state, to select the second structure in which the length is the longest with respect to each of the valve leaflets of the heart valve rendered in the plurality of medical images in the second state, to calculate the difference between the first structure and the second structure with respect to each of the valve leaflets of the heart valve, and to obtain the measurement result being the smallest value among the calculated differences, as the length over which the manipulation on the heart valve is possible. Consequently, the medical information processing apparatus 3 according to the first embodiment makes it possible to more accurately measure the measurement values related to the manipulation on the heart valve.

Further, according to the first embodiment, the calculating function 356 is configured to calculate the measurement value related to the contact part in the position of the cross-section at the first time point on the basis of: the structures of the plurality of tissues rendered on the cross-section set with the plurality of tissues at the second time point; and the structures of the plurality of tissues rendered on the cross-section set with the plurality of tissues at the first time point. Consequently, the medical information processing apparatus 3 according to the first embodiment makes it possible to easily perform the measuring process related to the structures of the tissues.

Further, according to the first embodiment, the controlling function 351 is configured to cause the display 33 to display the measurement values. Consequently, the medical information processing apparatus 3 according to the first embodiment makes it possible to provide the user with the measurement values.

Further, according to the first embodiment, the calculating function 356 is configured to calculate the measurement value related to the contact part between the plurality of tissues, with respect to each of the plurality of cross-sections set with the plurality of tissues. Consequently, the medical information processing apparatus 3 according to the first embodiment makes it possible to calculate the measurement values with respect to the entire contact part between the tissues.

Further, according to the first embodiment, the controlling function 351 is configured to cause the display 33 to display the display information based on the measurement values measured in the positions of the plurality of cross-sections. Consequently, the medical information processing apparatus 3 according to the first embodiment makes it possible to provide the user with the measurement values with respect to the entire contact part between the tissues.

Further, according to the first embodiment, the controlling function 351 is configured to cause the display information to be displayed over the graph indicating the measurement values respectively corresponding to the positions of the plurality of cross-sections, the display information indicating the threshold value used for judging the measurement values. Consequently, the medical information processing apparatus 3 according to the first embodiment makes it possible to provide the user with the various types of reference information related to the measurement values.

Further, according to the first embodiment, the controlling function 351 is configured to cause the input screen to be displayed, to receive the input regarding either the distance or the percentage numerical value being set on the basis of the feature points of the plurality of tissues, as the condition of the cross-section positions set with the plurality of tissues. Consequently, the medical information processing apparatus 3 according to the first embodiment makes it possible to easily set the cross-sections.

Further, according to the first embodiment, the controlling function 351 is configured to display the input screen used for selecting the representative value of the structures of the plurality of tissues segmented from each of the plurality of medical images taken in the first state and the representative value of the structures of the plurality of tissues segmented from each of the plurality of medical images taken in the second state. Consequently, the medical information processing apparatus 3 according to the first embodiment makes it possible to easily set the desired representative values.

Further, according to the first embodiment, the controlling function 351 is configured to cause at least one of the following to be displayed: the statistical information based on the measurement values; the graph indicating the measurement values respectively corresponding to the positions of the plurality of cross-sections; and the display image indicating, within the medical image, the information based on the measurement values respectively corresponding to the positions of the plurality of cross-sections. Consequently, the medical information processing apparatus 3 according to the first embodiment makes it possible to provide, in the various forms, the information about the measurement values with respect to the entire contact part between the tissues.

Further, according to the first embodiment, the segmenting function 355 is configured to obtain the structures of the plurality of tissues from certain medical images among the medical images of which the image quality exceeds the predetermined state. Consequently, the medical information processing apparatus 3 according to the first embodiment makes it possible to perform the calculation only on sources having a high reliability.

Further, according to the first embodiment, the segmenting function 355 is configured to obtain the structures of the plurality of tissues in the positions of the cross-sections determined on the basis of a medical image that renders the plurality of tissues but is of a type different from that of the medical images. Consequently, the medical information processing apparatus 3 according to the first embodiment makes it possible to easily provide the information desired by the user.

Further, according to the first embodiment, the segmenting function 355 is configured to obtain the structures of the plurality of tissues either two-dimensionally or three-dimensionally. Consequently, the medical information processing apparatus 3 according to the first embodiment makes it possible to reduce the processing loads in accordance with situations.

Other Embodiments

In the embodiments described above, the example was explained in which the structures of interest (e.g., the anterior cusp and the posterior cusp of the mitral valve) are segmented from each of the plurality of medical images obtained in each of the different states, so as to select the representative value for each of the states from the segmented structures of interest; however, possible embodiments are not limited to this example. For instance, it is also acceptable to select, for each of the states, one medical image from among the plurality of medical images, so as to calculate the length from the selected medical image.

For example, when the medical images at t1 to t6 illustrated in FIG. 3 are obtained, the judging function 353 at first determines that the medical images at t1 and t6 correspond to the open state and determines that the medical images at t2 to t5 correspond to the closed state, as the states of the medical images. Subsequently, on the basis of a condition arbitrarily set, the judging function 353 selects one of the medical images with respect to each of the states. In other words, on the basis of the condition, the judging function 353 selects either t1 or t6 for the medical image in the open state. Also, on the basis of the condition, the judging function 353 selects one from among the time points t2 to t5 for the medical image in the closed state.

In this situation, examples of the selection condition used for selecting the medical images include the image quality of the medical images, the cardiac phases in which the medical images were taken, and a designation operation performed by the user.

When the judging function 353 has selected the medical image for each of the states as described above, the setting function 354 sets a cross-section in each of the two selected medical images. After that, the segmenting function 355 segments the structures of interest, so that the calculating function 356 calculates the measurement values of the structures of interest.

Further, in the embodiments described above, the example was explained in which the measuring process related to the contact part is performed on the mitral valve; however, possible embodiments are not limited to this example. In other words, it is acceptable to use any site which has structures including a plurality of tissues and a plurality of states and in which the structures including the plurality of tissues can be in contact with each other. For example, it is acceptable to perform the processes on another heart valve such as the aortic valve, the tricuspid valve, or the pulmonary valve. In other examples, the processes may be performed on the throat, an eyelid, the mouth, or the like.

Further, in the embodiments described above, the example was explained in which the display 33 of the medical information processing apparatus 3 is caused to display the information about the measurement values related to the contact part; however, possible embodiments are not limited to this example. For instance, it is acceptable to cause a display of another apparatus connected to a network to display the information about the measurement values related to the contact part.

Further, in the embodiments described above, the example was explained in which the medical information processing apparatus 3 performs the processes; however, possible embodiments are not limited to this example. For instance, it is also acceptable to use a computer configuration of a server-client type, so as to perform a part of the calculations on the server side.

In the embodiments described above, the example was explained in which the image obtaining unit, the structure obtaining unit, the calculating unit, and the display controlling unit of the present disclosure are realized by using the image obtaining function, the segmenting function, the calculating function, and the controlling function of the processing circuitry, respectively; however, possible embodiments are not limited to this example. For instance, instead of realizing the image obtaining unit, the structure obtaining unit, the calculating unit, and the display controlling unit of the present disclosure by using the image obtaining function, the segmenting function, the calculating function, and the controlling function as described in the embodiments, it is also acceptable to realize the functions by using only hardware, only software, or a combination of hardware and software.

Further, the term "processor" used in the description of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). Alternatively, instead of having the programs saved in the storage circuit, it is also acceptable to directly incorporate the programs in the circuitry of one or more processors. In that situation, the one or more processors realizes the functions by reading and executing the programs incorporated in the circuitry thereof. Further, the processors of the present embodiment do not each necessarily have to be structured as a single circuit. It is also acceptable to structure one processor by combining together a plurality of independent circuits so as to realize the functions thereof.

Further, a medical information processing program executed by the one or more processors is provided as being incorporated in advance in a Read-Only Memory (ROM), a storage circuit, or the like. Alternatively, the medical information processing program may be provided as being recorded on a non-transitory computer-readable storage medium such as a Compact Disk Read-Only Memory (CD-ROM), a flexible disk (FD), a Compact Disk Recordable (CD-R), a Digital Versatile Disk (DVD), or the like, in a file that is in an installable format or in an executable format for these devices. Further, the medical information processing program may be stored in a computer connected to a network such as the Internet so as to be provided or distributed as being downloaded via the network. For example, the medical information processing program is structured by using modules including the processing functions described above. In the actual hardware, the modules are loaded into a main memory device when a CPU reads and executes the medical information processing program from a storage medium such as a ROM, so that modules are generated in the main memory device.

Further, in the embodiments and the modification examples described above, the constituent elements of the apparatuses illustrated in the drawings are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, with regard to the processes explained in the embodiments and the modification examples described above, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to accurately perform the measuring process relevant to the contact part.

In relation to the above embodiments, the following notes are presented as certain aspects and selectable characteristics of the present disclosure.

Note 1:

A medical information processing apparatus comprising:
an image obtaining unit configured to obtain medical images taken at a plurality of points in time;
a structure obtaining unit configured to obtain structures of a plurality of tissues, from medical images taken at a first point in time and at a second point in time different from the first point in time among the plurality of points in time; and
a calculating unit configured to calculate a measurement value related to a contact part between the plurality of tissues at the first point in time, on the basis of the structures of the plurality of tissues at the second point in time and the structures of the plurality of tissues at the first point in time obtained by the structure obtaining unit.

Note 2:

From the medical images taken at the first point in time at which the plurality of tissues are in a first state and taken at the second point in time at which the plurality of tissues are in a second state different from the first state, the structure obtaining unit may obtain the structures of the plurality of tissues in the first state and in the second state, respectively.

On the basis of the structures of the plurality of tissues in the second state and the structures of the plurality of tissues in the first state, the calculating unit may calculate the measurement value related to the contact part between the plurality of tissues in the first state.

Note 3:

The structure obtaining unit may segment, on the basis of features of the structures, each of the plurality of tissues from among the plurality of tissues rendered in each of a plurality of medical images taken in the first state and may segment, on the basis of features of the structures, each of the plurality of tissues from among the plurality of tissues rendered in each of a plurality of medical images taken in the second state.

On the basis of the structures of the plurality of tissues segmented from the plurality of medical images taken in the first state and the structures of the plurality of tissues segmented from the plurality of medical images taken in the second state, the calculating unit may calculate the measurement value related to the contact part between the plurality of tissues in the first state.

Note 4:

The plurality of tissues may be valve leaflets of a heart valve.

The structure obtaining unit may obtain the structures of the valve leaflets of the heart valve rendered in the medical image in the first state, which is a state in which the heart valve is closed and may obtain the structures of the valve leaflets of the heart valve rendered in the medical image in the second state, which is a state in which the heart valve is open.

The calculating unit may calculate the measurement value related to the contact part of the heart valve in the first state, on the basis of: a length related to the structures of the valve leaflets in the first state; and a length related to the structures of the valve leaflets in the second state.

Note 5:

The calculating unit may calculate the length of the contact part of the heart valve, on the basis of: the length from a contact start point to the annulus with respect to each of the valve leaflets of the heart valve rendered in the medical image in the first state; and the length of each of the valve leaflets of the heart valve rendered in the medical image in the second state.

Note 6:

The structure obtaining unit may obtain the structures of the valve leaflets of the heart valve rendered in a plurality of medical images in the first state and may obtain the structures of the valve leaflets of the heart valve rendered in a plurality of medical images in the second state.

The calculating unit may calculate the length of the contact part of the heart valve, on the basis of: the shortest length from the contact start point to the annulus with respect to each of the valve leaflets of the heart valve rendered in the plurality of medical images in the first state; and the longest length from the annulus to the valve tip end with respect to each of the valve leaflets of the heart valve rendered in the plurality of medical images in the second state.

Note 7:

The structure obtaining unit may obtain the structures of the valve leaflets of the heart valve rendered in a plurality of medical images in the first state and may obtain the structures of the valve leaflets of the heart valve rendered in a plurality of medical images in the second state.

The calculating unit may select the length from the contact start point to the annulus of a first valve leaflet among the valve leaflets of the heart valve in the first state, from within a first medical image among the plurality of medical images, may obtain the length from the contact start point to the annulus of a second valve leaflet different from the first valve leaflet, from the first medical image, and may calculate the length of the contact part of the heart valve, on the basis of: the length from the contact start point to the annulus of the first valve leaflet; the length from the contact start point to the annulus of the second valve leaflet; and the length from the annulus to the valve tip end of the first valve leaflet and the length from the annulus to the valve tip end of the second valve leaflet selected from within the plurality of medical images in the second state.

Note 8:

With respect to each of the valve leaflets of the heart valve rendered in the plurality of medical images in the first state, the calculating unit may select a first structure in which the length from the contact start point to the annulus of the valve leaflet is shortest. With respect to each of the valve leaflets of the heart valve rendered in the plurality of medical images in the second state, the calculating unit may select a second structure in which the length is longest. With respect to each of the valve leaflets of the heart valve, the calculating unit may calculate the difference between the first structure and the second structure. The calculating unit may obtain a measurement result being the smallest value among the calculated differences, as the length of the contact part of the heart valve.

Note 9:

The calculating unit may calculate the length related to the contact part of the heart valve, on the basis of: the length from a point having the largest curvature to the annulus with respect to each of the valve leaflets of the heart valve rendered in the medical image in the first state; and the length from the annulus to the valve tip end with respect to each of the valve leaflets of the heart valve rendered in the medical image in the second state.

Note 10:

The structure obtaining unit may obtain the structures of the valve leaflets of the heart valve rendered in a plurality of medical images in the first state and may obtains the structures of the valve leaflets of the heart valve rendered in a plurality of medical images in the second state.

The calculating unit may calculate a length over which a manipulation on the heart valve is possible on the basis of: the shortest length from the point having the largest curvature to the annulus with respect to each of the valve leaflets of the heart valve rendered in the plurality of medical images in the first state; and the longest length from the annulus to the valve tip end with respect to each of the valve leaflets of the heart valve rendered in the plurality of medical images in the second state.

Note 11:

With respect to each of the valve leaflets of the heart valve rendered in the plurality of medical images in the first state, the calculating unit may select a first structure in which the length from the point having the largest curvature to the annulus of the valve leaflet is shortest. With respect to each of the valve leaflets of the heart valve rendered in the plurality of medical images in the second state, the calculating unit may select a second structure in which the length is longest. With respect to each of the valve leaflets of the heart valve, the calculating unit may calculate the difference between the first structure and the second structure and may obtain a measurement result being the smallest value among the calculated differences as the length over which the manipulation on the heart valve is possible.

Note 12:

On the basis of the structures of the plurality of tissues rendered on a cross-section set with the plurality of tissues at the second point in time and the structures of the plurality of tissues rendered on a cross-section set with the plurality of tissues at the first point in time, the calculating unit may calculate the measurement value related to the contact part in the position of the cross-section at the first point in time.

Note 13:

A display controlling unit configured to cause a display unit to display the measurement value may further be provided.

Note 14:

The calculating unit may calculate the measurement value related to the contact part between the plurality of tissues, with respect to each of two or more cross-sections set with the plurality of tissues.

Note 15:

A display controlling unit configured to cause a display unit to display display information based on the measurement values measured in the positions of the two or more cross-sections may further be provided.

Note 16:

The display controlling unit may cause the display information to be displayed over a graph indicating the measurement values respectively corresponding to the positions of the two or more cross-sections, the display information indicating a threshold value used for judging the measurement values.

Note 17:

The display controlling unit may cause at least one of the following to be displayed: statistical information based on the measurement values; a graph indicating the measurement values respectively corresponding to the positions of the plurality of cross-sections; and a display image indicating, within the medical image, the information based on the measurement values respectively corresponding to the positions of the plurality of cross-sections.

Note 18:

A display controlling unit may further be provided so as to display an input screen used for receiving an input regarding either the distance or the percentage numerical value being set on the basis of the feature points of the plurality of tissues, as the condition of the cross-section positions set with the plurality of tissues.

Note 19:

A display controlling unit may further be provided so as to display an input screen used for selecting a representative value of the structures of the plurality of tissues segmented from each of the plurality of medical images taken in the first state and a representative value of the structures of the plurality of tissues segmented from each of the plurality of medical images taken in the second state.

Note 20:

The structure obtaining unit may judge image quality of the medical images and may obtain the structures of the plurality of tissues from certain medical images of which the image quality exceeds a predetermined state.

Note 21:

The structure obtaining unit may determine the positions of the cross-sections on the basis of a medical image that renders the plurality of tissues but is of a type different from that of the medical images.

Note 22:

The structure obtaining unit may obtain the structures of the plurality of tissues either two-dimensionally or three-dimensionally.

Note 23:

A medical information processing method including:
obtaining medical images taken at a plurality of points in time;
obtaining structures of a plurality of tissues, from medical images taken at a first point in time and at a second point in time different from the first point in time among the plurality of points in time; and
calculating a measurement value related to a contact part between the plurality of tissues at the first point in time, on the basis of the obtained structures of the plurality of tissues at the second point in time and the obtained structures of the plurality of tissues at the first point in time.

Note 24:

A non-transitory storage medium storing therein a program that causes a computer to execute:
obtaining medical images taken at a plurality of points in time;
obtaining structures of a plurality of tissues, from medical images taken at a first point in time and at a second point in time different from the first point in time among the plurality of points in time; and
calculating a measurement value related to a contact part between the plurality of tissues at the first point in time, on the basis of the obtained structures of the plurality of tissues at the second point in time and the obtained structures of the plurality of tissues at the first point in time.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
processing circuitry configured to
obtain medical images taken at a plurality of points in time;
obtain structures of valve leaflets of a heart valve rendered in a medical image taken at a first point in time among the plurality of points in time, the first point in time being a point in time at which the heart valve is in a first state, which is a state in which the heart valve is closed;
obtain the structures of the valve leaflets of the heart valve rendered in a medical image taken at a second point in time among the plurality of points in time, the second point in time being a point in time at which the heart valve is in a second state, which is a state in which the heart valve is open; and
calculate a measurement value related to a contact part between the valve leaflets of the heart valve in the first state, on a basis of: a length related to the structures of the valve leaflets of the heart valve in the first state; and a length related to the structures of the valve leaflets of the heart valve in the second state.

2. The medical information processing apparatus according to claim 1, wherein
the processing circuitry is configured to
obtain each of the structures of the valve leaflets of the heart valve rendered in each of a plurality of medical images taken in the first state,
obtain each of the structures of the valve leaflets of the heart valve rendered in each of a plurality of medical images taken in the second state,
select, on a basis of features of the structures, a first structure from among the structures of the valve leaflets of the heart valve segmented from each of the plurality of medical images taken in the first state,
select, on a basis of features of the structures, a second structure from among the structures of the valve leaflets of the heart valve segmented from the plurality of medical images taken in the second state, and
calculate the measurement value related to the contact part between the valve leaflets of the heart valve in the first state, on a basis of the first structure and the second structure.

3. The medical information processing apparatus according to claim 1, wherein the processing circuitry is configured to calculate a length of the contact part between the valve leaflets of the heart valve, on a basis of: a length from a contact start point to an annulus with respect to each of the valve leaflets of the heart valve rendered in the medical image in the first state; and a length from the annulus to a valve tip end with respect to each of the valve leaflets of the heart valve rendered in the medical image in the second state.

4. The medical information processing apparatus according to claim 3, wherein
the processing circuitry is configured to
obtain the structures of the valve leaflets of the heart valve rendered in a plurality of medical images in the first state, obtain the structures of the valve leaflets of the heart valve rendered in a plurality of medical images in the second state, select the length from the contact start point to the annulus of a first valve leaflet among the valve leaflets of the heart valve in the first state, from within a first medical image among the plurality of medical images, obtain the length from the contact start point to the annulus of a second valve leaflet different from the first valve leaflet, from the first medical image, and calculate the length of the contact part between the valve leaflets of the heart valve, on a basis of: the length from the contact start point to the annulus of the first valve leaflet; the length from the contact start point to the annulus of the second valve leaflet; and the length from the annulus to the valve tip end of the first valve leaflet and the length from the annulus to the valve tip end of the second valve leaflet selected from within the plurality of medical images in the second state.

5. The medical information processing apparatus according to claim 3, wherein the processing circuitry is configured to obtain the structures of the valve leaflets of the heart valve rendered in a plurality of medical images in the first state, obtain the structures of the valve leaflets of the heart valve rendered in a plurality of medical images in the second state, and calculate the length of the contact part between the valve leaflets of the heart valve, on a basis of: a shortest length from the contact start point to the annulus with respect to each of the valve leaflets of the heart valve rendered in the plurality of medical images in the first state; and a longest length from the annulus to the valve tip end with respect to each of the valve leaflets of the heart valve rendered in the plurality of medical images in the second state.

6. The medical information processing apparatus according to claim 5, wherein the processing circuitry is configured to select, with respect to each of the valve leaflets of the heart valve rendered in the plurality of medical images in the first state, a first structure in which the length from the contact start point to the annulus of the valve leaflet is shortest, select, with respect to each of the valve leaflets of the heart valve rendered in the plurality of medical images in the second state, a second structure in which the length is longest, calculate, with respect to each of the valve leaflets of the heart valve, a difference between the first structure and the second structure, and obtain a measurement result being a smallest value among the calculated differences, as the length of the contact part between the valve leaflets of the heart valve.

7. The medical information processing apparatus according to claim 1, wherein the processing circuitry is configured to calculate the length related to the contact part between the valve leaflets of the heart valve, on a basis of: a length from a point having a largest curvature to an annulus with respect to each of the valve leaflets of the heart valve rendered in the medical image in the first state; and a length from the annulus to a valve tip end with respect to each of the valve leaflets of the heart valve rendered in the medical image in the second state.

8. The medical information processing apparatus according to claim 7, wherein the processing circuitry is configured to obtain the structures of the valve leaflets of the heart valve rendered in a plurality of medical images in the first state, obtain the structures of the valve leaflets of the heart valve rendered in a plurality of medical images in the second state, and calculate a length over which a manipulation on the heart valve is possible on a basis of: a shortest length from the point having the largest curvature to the annulus with respect to each of the valve leaflets of the heart valve rendered in the plurality of medical images in the first state; and a longest length from the annulus to the valve tip end with respect to each of the valve leaflets of the heart valve rendered in the plurality of medical images in the second state.

9. The medical information processing apparatus according to claim 8, wherein the processing circuitry is configured to select, with respect to each of the valve leaflets of the heart valve rendered in the plurality of medical images in the first state, a first structure in which the length from the point having the largest curvature to the annulus of the valve leaflet is shortest, select, with respect to each of the valve leaflets of the heart valve rendered in the plurality of medical images in the second state, a second structure in which the length is longest, calculate, with respect to each of the valve leaflets of the heart valve, a difference between the first structure and the second structure, and obtain a measurement result being a smallest value among the calculated differences as the length over which the manipulation on the heart valve is possible.

10. The medical information processing apparatus according to claim 1, wherein the processing circuitry is configured to calculate, on a basis of the structures of the valve leaflets of the heart valve rendered on a cross-section set with the valve leaflets of the heart valve at the second point in time and the structures of the valve leaflets of the heart valve rendered on a cross-section set with the valve leaflets of the heart valve at the first point in time, the measurement value related to the contact part in a position of the cross-section at the first point in time.

11. The medical information processing apparatus according to claim 1, wherein the processing circuitry is configured to cause a display to display the measurement value.

12. The medical information processing apparatus according to claim 10, wherein the processing circuitry is configured to calculate the measurement value related to the contact part between the valve leaflets of the heart valve, with respect to each of two or more of the cross-sections set with the valve leaflets of the heart valve.

13. The medical information processing apparatus according to claim 12, wherein the processing circuitry is configured to cause a display to display display information based on the measurement values measured in positions of the two or more cross-sections.

14. The medical information processing apparatus according to claim 13, wherein the processing circuitry is configured to cause the display to display the display information to be displayed over a graph indicating the measurement values respectively corresponding to the positions of the two or more cross-sections, the display information indicating a threshold value used for judging the measurement values.

15. The medical information processing apparatus according to claim 1, wherein the processing circuitry is configured to obtain the structures of the valve leaflets of the heart valve from certain medical images among the medical images of which image quality exceeds a predetermined state.

16. The medical information processing apparatus according to claim 10, wherein the processing circuitry is configured to obtain the structures of the valve leaflets of the heart valve in the positions of the cross-sections determined on a basis of a medical image that renders the valve leaflets of the heart valve but is of a type different from that of the medical images.

17. The medical information processing apparatus according to claim 1, wherein the processing circuitry is configured to obtain the structures of the valve leaflets of the heart valve either two-dimensionally or three-dimensionally.

18. The medical information processing apparatus according to claim 1, wherein
the processing circuitry is configured to
obtain the structures of the valve leaflets of the heart valve rendered in a plurality of medical images taken in the first state, and
calculate, as the length related to the structures of the valve leaflets of the heart valve in the first state, an average length from a contact start point to an annulus with respect to each of the valve leaflets of the heart valve rendered in the plurality of medical images taken in the first state.

19. The medical information processing apparatus according to claim 1, wherein
the processing circuitry is configured to
obtain the structures of the valve leaflets of the heart valve rendered in a plurality of medical images taken in the second state, and
calculate, as the length related to the structures of the valve leaflets of the heart valve in the second state, an average length from an annulus to a valve tip end with respect to each of the valve leaflets of the heart valve rendered in the plurality of medical images taken in the second state.

20. A medical information processing method comprising:
obtaining medical images taken at a plurality of points in time;
obtaining structures of valve leaflets of a heart valve rendered in a medical image taken at a first point in time among the plurality of points in time, the first point in time being a point in time at which the heart valve is in a first state, which is a state in which the heart valve is closed;
obtaining the structures of the valve leaflets of the heart valve rendered in a medical image taken at a second point in time among the plurality of points in time, the second point in time being a point in time at which the heart valve is in a second state, which is a state in which the heart valve is open; and
calculating a measurement value related to a contact part between the valve leaflets of the heart valve in the first state, on a basis of: a length related to the structures of the valve leaflets of the heart valve in the first state; and a length related to the structures of the valve leaflets of the heart valve in the second state.

21. A non-transitory storage medium storing therein a program that causes a computer to execute:
obtaining medical images taken at a plurality of points in time;
obtaining structures of valve leaflets of a heart valve rendered in a medical image taken at a first point in time among the plurality of points in time, the first point in time being a point in time at which the heart valve is in a first state, which is a state in which the heart valve is closed;
obtaining the structures of the valve leaflets of the heart valve rendered in a medical image taken at a second point in time among the plurality of points in time, the second point in time being a point in time at which the heart valve is in a second state, which is a state in which the heart valve is open; and
calculating a measurement value related to a contact part between the valve leaflets of the heart valve in the first state, on a basis of: a length related to the structures of the valve leaflets of the heart valve in the first state; and a length related to the structures of the valve leaflets of the heart valve in the second state.

22. A medical information processing apparatus comprising:
processing circuitry configured to
obtain medical images taken at a plurality of points in time;
obtain structures of a plurality of tissues, from medical images taken at a first point in time and at a second point in time different from the first point in time among the plurality of points in time; and
calculate a measurement value related to a contact part between the plurality of tissues at the first point in time, on a basis of the obtained structures of the plurality of tissues at the second point in time and the obtained structures of the plurality of tissues at the first point in time, wherein
the processing circuitry is configured to
calculate the measurement value related to the contact part between the plurality of tissues, with respect to each of two or more of cross-sections set with the plurality of tissues; and
cause a display to display display information to be displayed over a graph indicating the measurement values respectively corresponding to positions of the two or more cross-sections, the display information indicating a threshold value used for judging the measurement values.

23. A medical information processing method comprising:
obtaining medical images taken at a plurality of points in time;
obtaining structures of a plurality of tissues, from medical images taken at a first point in time and at a second point in time different from the first point in time among the plurality of points in time;
calculating a measurement value related to a contact part between the plurality of tissues at the first point in time, on a basis of the obtained structures of the plurality of tissues at the second point in time and the obtained structures of the plurality of tissues at the first point in time, wherein calculating the measurement value comprises calculating the measurement value related to the contact part between the plurality of tissues, with respect to each of two or more of cross-sections set with the plurality of tissues; and
causing a display to display display information to be displayed over a graph indicating the measurement values respectively corresponding to positions of the two or more cross-sections, the display information indicating a threshold value used for judging the measurement values.

24. A non-transitory storage medium storing therein a program that causes a computer to execute:

obtaining medical images taken at a plurality of points in time;

obtaining structures of a plurality of tissues, from medical images taken at a first point in time and at a second point in time different from the first point in time among the plurality of points in time;

calculating a measurement value related to a contact part between the plurality of tissues at the first point in time, on a basis of the obtained structures of the plurality of tissues at the second point in time and the obtained structures of the plurality of tissues at the first point in time, wherein calculating the measurement value comprises calculating the measurement value related to the contact part between the plurality of tissues, with respect to each of two or more of cross-sections set with the plurality of tissues; and causing a display to display display information to be displayed over a graph indicating the measurement values respectively corresponding to positions of the two or more cross-sections, the display information indicating a threshold value used for judging the measurement values.

* * * * *